United States Patent [19]

Imaki et al.

[11] Patent Number: 4,843,094
[45] Date of Patent: Jun. 27, 1989

[54] DERIVATIVES OF P-GUANTIDINOBENZOIC ACID AND PHARMACEUTICAL AGENTS CONTAINING THEM AS ACTIVE INGREDIENT

[75] Inventors: Katsuhiro Imaki, Kyoto; Yoshinobu Arai, Osaka; Hiroyuki Ohno, Shiga, all of Japan

[73] Assignee: Ono Pharmaceutical Co., Ltd., Osaka, Japan

[21] Appl. No.: 929,317

[22] Filed: Nov. 12, 1986

[51] Int. Cl.⁴ ............... A61K 31/255; C07C 143/68
[52] U.S. Cl. ................................ 514/518; 514/517; 558/58; 560/34
[58] Field of Search ............... 558/58; 560/34; 514/517, 518

[56] References Cited

U.S. PATENT DOCUMENTS

| | | | |
|---|---|---|---|
| 3,520,918 | 7/1970 | Chase et al. | 260/471 |
| 4,359,046 | 11/1982 | Shaw, Jr. | 128/130 |
| 4,423,069 | 12/1983 | Kaminski et al. | 424/310 |

FOREIGN PATENT DOCUMENTS

| | | |
|---|---|---|
| 0170180 | 7/1985 | European Pat. Off. |
| 1905813 | 2/1969 | Fed. Rep. of Germany |
| 2150802 | 4/1973 | France |
| 2456731 | 5/1979 | France |
| 2450251 | 2/1980 | France |
| 2007653 | 10/1978 | United Kingdom |
| 2057435 | 8/1980 | United Kingdom |

OTHER PUBLICATIONS

Chemical Abstracts, vol.93, No. 5, 4th Aug. 1980, p. 393, No. 40319n, Columbus, Ohio, U.S.; N. Masayuki et al.: "Inverse Substrates", Part VII.
"Inverse Substrates", for Trypsin–Like Enzymes & J. Pharmacobio-Dyn. 1980, 3(4), 213-19.
Chemical Abstracts, vol. 94, No. 15, Apr. 13th 1981, p. 661, No. 121139b, Columbus, Ohio, U.S.; & JP-A-80 100 356 (Kowa Co., Ltd) 31-07-1980.
Biochimica et Biophysica Acta, vol. 661, 1981, pp. 342-345, Elsevier/North-Holland Biomedical Press; S. Fuji et al. "New Synthetic Inhibitors of Clr., Cl Esterase, Thrombin, Plasmin, Kallikrein and Trypsin".
Journal of Medicinal Chemistry, vol. 29, No. 4, Apr. 1986, pp. 514–519, American Chemical Society, Washington, D.C., U.S.; J. M. Kaminski et al.: "Synthesis and Inhibition of Human Acrosin and Trypsin and Acute Toxicity of Aryl 4–Guanidinobenzoates".

*Primary Examiner*—Mary C. Lee
*Assistant Examiner*—Bernard I. Dentz
*Attorney, Agent, or Firm*—Sughrue, Mion, Zinn, Macpeak, and Seas

[57] ABSTRACT

Compounds presented by the general formula:

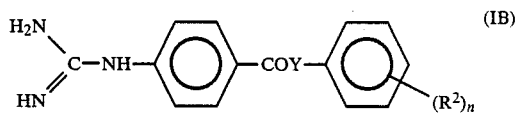

[wherein when Y is oxygen, $R^2$ is H, alkyl, alkoxy, alkoxymethyl, $-COOR^3$, $-CH_2COOR^3$, $-CH=CH-COOR^3$, halogen, $-CF_3$, $-COR^4$, $-OCOR^4$, $-CH_2OCOR^4$, $-SO_2R^4$, $-OSO_2R^4$, $-CONR^5R^6$, $-SO_2NR^5R^6$, $-CONH-SO_2NR^5R^6$, $-NHSO_2R^7$, $-NO_2$, $-OH$, $-CH_2OH$, guanidino, benzyloxy, guanidinophenylthiomethyl, morpholinosulfonylphenoxymethyl, pyridyloxymethyl, or (1,1-dioxothiazol-3-yl)carbonyl, or when Y is sulfur, $R^2$ is H, alkyl, alkoxy, halogen, $-COOR^3$, $-CH_2COOR^3$, $-NO_2$, or $-SO_2NR^5R^6$, and n represents an integer of one to five, and when n represents more than two, each of $R^2$ may be the same group or the different group.] and acid addition salts thereof have inhibitory effect on elastase, and, therefore, are useful for the treatment and/or prevention of diseases induced by abnormal enhancing of degradation of proteins such as elastin and the like, by the action of elastase in mammals, especially in human beings.

3 Claims, No Drawings

DERIVATIVES OF P-GUANTIDINOBENZOIC ACID AND PHARMACEUTICAL AGENTS CONTAINING THEM AS ACTIVE INGREDIENT

DESCRIPTION

1. Field of the Invention

The present invention relates to derivatives of p-guanidinobenzoic acid and the pharmaceutical agents containing them as active ingredients.

More particularly, it relates to new derivatives of p-guanidinobenzoic acid of the general formula:

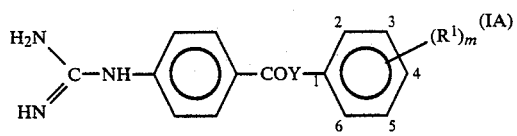

(wherein all symbols are the same meaning as described hereinafter.), and relates to elastase inhibitors containing, as active ingredient, derivatives of p-guanidinobenzoic acid of the general formula:

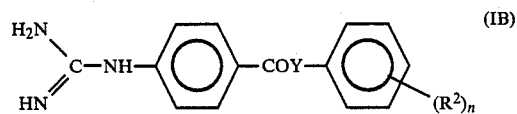

(wherein all symbols are the same meaning as described hereinafter.).

2. Background of Invention

Lysosomal hydrolases of neutrophils have an important role for an organism defense reaction against tissue damage caused by microbe or inflammation etc.

Elastase and cathepsin G, which belong to neutral serine proteinase locally existed in azurophil granule mainly play a part in decomposition of a connective tissue.

Especially, elastase degrades elastic connective tissue by cleaving the cross-linking of elastin which directly maintains the elasticity of lung tissue etc., and by cleaving hydrophobic part of protein [J. Cell. Biol., 40, 366 (1969)] and degrades the cross-linking area of collagen selectively [J. Biochem., 84, 559 (1978)], and it acts on such as proteoglycans etc. [J. Clin. Invest., 57, 615 (1976)].

Elastase is inactivated by $\alpha_1$-proteinase inhibitor ($\alpha_1$-PI) that is natural occurring inhibitor for serine, proteinase in vivo and the unbalance of enzyme and inhibitor system causes the destruction of the tissue [Schweiz. Med. Wshr., 114, 895 (1984)].

The turnover of elastin in normal tissue is very slow [Endocrinology, 120, 92 (1978)], but the pathological acceleration in degradation of elastin is found under various unsound state such as pulmonary emphysema [Am. Rev. Respir. Dis., 110, 254 (1974)], atherosclerosis [Lab. Invest., 22, 228 (1970)] and rheumatoid arthritis [in Neutral Proteases of Human Polymorphonuclear Leukocytes, Urban and Schwarzenberg, Baltimore - Munich (1978), page 390], suggesting the relationship of elastase and diseases [Infection·Inflammation·Immunity, 13, 13 (1983)].

PRIOR ART

Under the background as mentioned above, recently the studies and development on elastase inhibitors have been conducted heartily, various substances inhibiting elastase have been proposed and many patent applications have been filed. However, elastase inhibitors consisting of derivatives of p-guanidinobenzoic acid, as shown in the present invention, have not been known at all till now.

On the other hand, heretofore the various esters of p-guanidinobenzoic acid have been known. For example, when Y is an oxygen atom in the general formulae (IA) and (IB)

(1) in the specification of Japanese Patent Kokoku No. 54-40534, the compounds of the general formula:

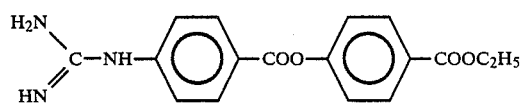

has been disclosed, (2) in the specification of Japanese Patent Kokai No. 50-4038, the compounds of the general formula:

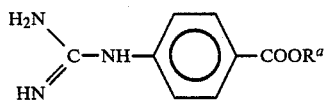

(wherein $R^a$ represents an aromatic group, and an said aromatic group may be substituted by a lower alkyl group, a lower alkoxycarbonyl group, a carboxyl group, a carboxy lower alkyl group, a carboethoxy lower alkyl group, a lower alkoxy group, an acylamido group or a carbamoyl group)

(abstracted related points) have been disclosed, (3) in the specification of Japanese Patent Kokoku No. 57-35870, the compounds of the general formula:

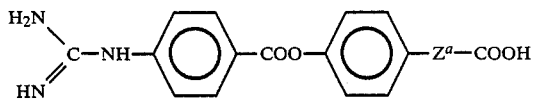

(wherein $Z^a$ represents the group selected from the group consist of a carbon- carbon covalent bond, a methylene group, an ethylene group and a vinylene group) have been disclosed, (4) in the specification of Japanese Patent Kokai No. 55-55154, the compounds of the general formula:

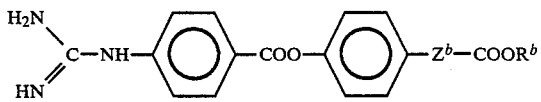

(wherein $Z^b$ represents a methylene group, an ethylene group or a vinylene group, and $R^b$ represents a lower alkyl group.) have been disclosed, (5) in the specification of Germany Patent Publication No. 3005580, the compounds represent by the general formula:

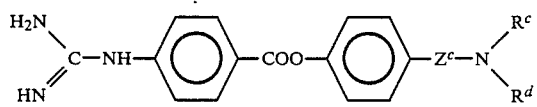

(wherein $Z^c$ represents a sulfonyl group or the group represented by $Z^d$-CO, $Z^d$ represents a bond, methylene, ethylene or vinylene, $R^c$ and/or $R^d$ represent a hydrogen atom or a alkyl group.) have been disclosed, (6) in the specification of Germany Patent Publication No. 1905813, the compounds of the general formula:

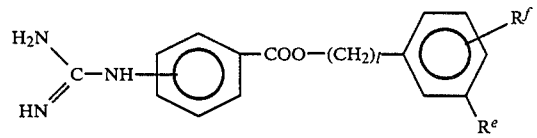

(wherein $R^e$ and/or $R^f$ represent a hydrogen atom; an alkyl group, an aryl group, a nitro group, an amino group, alkylamino group, a dialkylamino group, an alkoxy group, a carboxy group, a carboalkoxy group or a halogen atom, 1 represents an integer of zero or one.) have been disclosed.

(7) in the specification of U.S. Pat. No. 4,423,069, the method to inhibit conception by giving the compounds represented by the general formula:

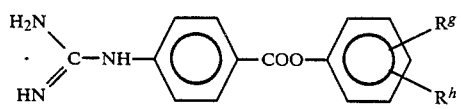

[wherein $R^g$ represents a halogen, a trihalomethyl, a nitryl group, a formyl group, $OR^i$, $COR^i$, $COOR^i$, $CONH_2$ or $CONR^jR^k$ (wherein $R^i$, $R^j$ or $R^k$ represent an alkyl group of one to eight carbon atoms), $R^h$ represents a hydrogen atom or the group represented by the symbol $R^g$.]

and a salt thereof have been disclosed, (8) In the specification of Japanese Patent Kokai No. 61-43151, the compounds represented by the general formula:

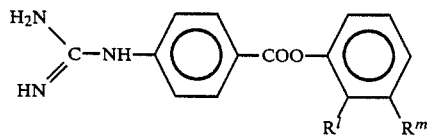

(wherein $R^l$ represents a hydrogen, a nitrile group or an ether group, $R^m$ represents a hydrogen, an ether group, an ester group or a carbamoyl group, except that $R^l$ and $R^m$ represent a hydrogen at the same time.)

and agents of depressing acrocine have been disclosed,

On the other hand, when Y is a sulfur atom, (9) In the specification of Japanese Patent Kokoku No. 55-42076, the compounds described by the general formula:

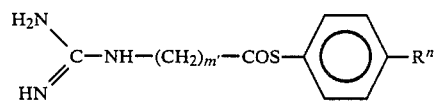

(wherein $R^n$ represents a hydrogen atom or an ethoxycarbonyl group and symbol M' represents an integer of four to six) have been disclosed,

(10) in the specification of Japanese Patent Kokoku No. 56-3345, the compounds described by the general formula:

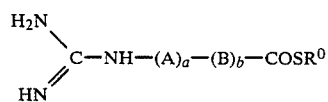

(wherein A represents a straight- or branched-chain alkylene group of one to ten carbon atoms, B represents p-phenylene group or divalent alicyclic group, symbol a represents zero or one, symbol b represents zero or one, the total number of a and b represent one or two, $R^o$ represents the group selected from the group of an ethoxycarbonyllkyl group of one to ten carbon atoms, the alicyclic group, a phenyl group, a naphtyl group and a phenylalkyl group and the alicyclic group and the aromatic group described above, may be replaced by a lower alkyl group, an ethoxycarbonyl group, an ethoxycarbonyl-lower alkyl group, a carboxyalkyl group, a halogen atom, an alkoxy group, an acylamino group, an alkylsulfonyl group, a carboxy group, a thiocarboxy group, a mercaptocarbonyl group, a nitro group or a carbamoyl group.) have been disclosed.

In the specification (1) to (6), (9) and (10) mentioned above, it is described that all these compounds have inhibitory effects on trypsin and plasmin, and therefore, are useful for the treatment of acute pancreatitis and bleeding diseases as anti-plasmin agents. And there is no description about an inhibitory effect of these compounds on elastase in the above specifications, nor report concerning about the examination of the effect so far.

Likewise, in the specifications (7) and (8) mentioned above, it is described that all compounds have inhibitory effects on acrocine etc. which are important enzymes in fertilization, and accordingly it is useful as the method for inhibition of conception and as an agent for inhibition of fertilization.

Elastase belongs to serine proteinase like trypsin and plasmin (hereinafter described "trypsin and plasmin" as "other serine proteinase" in order to distinguish from elastase), but is much different from them in point of enzymatic property and substrate specificity. Accordingly, it is reasonable to consider that elastase is a quite different enzyme group from other serine proteinase essentially, and therefore, the development of elastase inhibitors should be considered from a quite different point of view.

That is, elastase, especially human neutrophil elastase is a basic glycoprotein ["Protein Degradation in Health and Disease", edited by D. Evered and J. Whelan, page 51, Excerpta Medica, Amsterdam (1980)] having the molecular weight of about 30,000 [Biochem. J., 155, 255 (1976)], its isoelectric point being between pH 8.77 and 9.15 [Anal. Biochem., 90, 481 (1978)], and therefore, it is different from other serine proteinases in proteinic property.

Furthermore, in substrate specificity, elastase is classified as endopeptidases which mainly cleave a protein at the carboxy terminal of alanine residue. Even in this point, elastase is different from other serine proteinase. As said above, there is the fundamental differences between both enzyme, and therefore it is entirely impossible to analogize elastase inhibitors from other serine proteinase inhibitors.

PURPOSE OF THE INVENTION

As the result of energestic investigations in order to find new elastase inhibitory agents that have quite different chemical structure from conventional one, based on these findings, the present inventors have now found the fact that a kind of derivatives of p-guanidinobenzoic acid pheyl ester, known as inhibitory agents of other serine proteinase, unexpectedly has an inhibitory effect on elastase, then completed this invention.

The fact that inhibitory agents of other serine proteinase have been an inhibitory effect on elastase, has been confirmed experimentaly for the first time, and was never anticipated until now.

CONSTITUTION OF THE INVENTION

Accordingly, the present invention relates to the novel compounds, i.e. derivatives of p-guanidinobenzoic acid of the general formula:

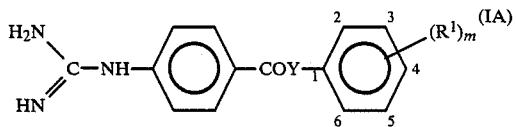

[wherein Y represents an oxygen atom or a sulfur atom and when Y is an oxygen atom, $(R^1)m$ represents the group selected from 2-methyl, 3-methyl, 2,3-dimethyl, 3,5-dimethyl, 3-ethyl, 2-methoxy, 3-methoxy, 4-methoxy, 3,5-dimethoxy, 5-etanesulfonyloxy-3-methoxymethyl, 3-hydroxy-5-methoxymethyl, 5-(4-guanidinobenzoyloxy)-3-methoxymethyl, 3-carboxy-2-chloro, 3,5-dicarboxy, 2-carboxy-5-chloro, 2-chloro-3-methoxycarbonyl, 2-chloro-4-methoxycarbonyl, 3-chloro-4-methoxycarbonyl, 5-chloro-2-methoxycarbonyl, 3-chloro-5-methoxycarbonyl, 3,5-bis(isopropoxycarbonyl), 5-chloro-2-isopropoxycarbonyl, 2-chloro-3-isopropoxycarbonyl, 3-sec-butoxycarbonyl-2-chloro, 3-methoxycarbonylmethyl, 2-chloro-3-methoxycarbonylmethyl, 2-chloro-4-methoxycarbonylmethyl, 3-chloro-4-methoxycarbonylmethyl, 4-(2-methoxycarbonylvinyl), 2-fluoro, 3-fluoro, 4-fluoro, 2,6-difluoro, 2,3-difluoro, 2,3,4,5,6-pentafluoro, 2-chloro, 3-chloro, 4-chloro, 2,5-dichloro, 2,6-dichloro, 3,5-dichloro, 3-chloro-5-methoxy, 4-chloro-3-methoxy, 2-chloro-5-methoxy, 2-bromo, 3-bromo, 4-iodo, 2-trifluoromethyl, 3-trifluoromethyl, 3,5-bistrifluoromethyl, 3-acetyl, 2-acetyl-5-methoxy, 2-acetyl-5-propoxy, 2-acetyl-5-chloro, 5-chloro-2-propionyl, 5-chloro-2-isobutyryl, 3-benzoyl, 4-benzoyl, 4-benzoyl-2-chloro, 4-benzoyl-2,3-dichloro, 5-chloro-2-cyclopentylacetyl, 3-acetoxy, 4-acetoxy, 5-acetoxy-3-chloro, 3-chloro-5-propionyloxy, 3-benzoyloxy, 3-(4-guanidinobenzoyloxy), 3,5-bis(4-guanidinobenzoyloxy), 3-acetyl-5-(4-guanidinobenzoyloxy), 5-(4-guanidinobenzoyloxy)-3-methoxycarbonyl, 3-chloro-5-(4-guanidinobenzoyloxy), 5-(4-guanidinobenzoyloxy)-3-methoxy, 5-(4-guanidinobenzoyloxy)-3-methyl, 5-acetoxymethyl-3-chloro, 4-mesyl, 5-mesyloxy-3-methoxy, 3-chloro-5-mesyloxy, 3-chloro-5-ethanesulfonyloxy, 3-chloro-5-isopropanesulfonyloxy, 5-benzenesulfonyloxy-3-chloro, 5-etanesulfonyloxy-3-methyl, 5-carbamoyl-3-chloro, 3-(N,N-dimethylcarbamoyl), 2-chloro-3-(N-methylcarbamoyl), 3-(4-guanidinobenzoyloxy)-5-(N-methylcarbamoyl), 3,5-bis(N-ethylcarbamoyl), 3,5-bis(N-propylcarbamoyl), 5-(N-benzylcarbamoyl)-3-(4-guanidinobenzoyloxy), 3-chloro-5-{N-(3-pyridyl)carbamoyl}, 3-chloro-5-(N,N-dimethylcarbamoyloxy), 3-chloro-5-(N-ethylcarbamoyloxy), 3-sulfamoyl, 3-chloro-4-(N,N-dimethylsulfamoyl), 2-(N,N-diethylsulfamoyl), 3-(N,N-diethylsulfamoyl), 4-(N,N-diethylsulfamoyl), 3-chloro-4-(N,N-diethylsulfamoyl), 3-chloro-5-(N,N-diethylsulfamoyl), 4-(N,N-diethylsulfamoyl)-2-fluoro, 4-(N,N-dipropylsulfamoyl), 4-(1-pyrrolidinylsulfonyl), 3-piperidinosulfonyl, 3-morpholinosulfonyl, 4-morpholinosulfonyl, 3-chloro-5-{N-(4-sulfamoylphenyl)carbamoyl}, 3-chloro-5-[N-{4-(N,N-dimethylsulfamoyl)phenyl}carbamoyl], 3-chloro-5-[N-{4-(N,N-diethylsulfamoyl)phenyl}carbamoyl], 2-chloro-5-(N-mesylamino), 3-chloro-5-(N-ethanesulfonylamino), 3-nitro, 4-nitro, 3-ydroxy-5-methyl, 5-hydroxy-3-methoxy, 5-hydroxy-3-methoxycarbonyl, 3-chloro-5-hydroxy, 3-(4-guanidinobenzoyloxy)-5-hydroxy, 5-hydroxy-3-(N-methylcarbamoyl), 3-(N-benzylcarbamoyl)-5-hydroxy, 3-chloro-5-hydroxymethyl, 3-guanidino, 4-guanidino, 2-chloro-5-guanidino, 5-benzyloxy-3-chloro, 3-chloro-5-(4-guanidinophenylthiomethyl), 3-chloro-5-(4-morpholinosulfonyl)phenoxymethyl, 3-methoxy-5-(4-morpholinosulfonyl)phenoxymethyl, 3-chloro-5-(3-pyridyl)oxymethyl, 3-methoxy-5-(1,1-dioxothiazol-3-yl)carbonyl and 3-chloro-5-(1,1-dioxothiazol-3-yl)carbonyl group.

(ii) when Y is a sulfur atom, $(R^1)m$ represents the group slected from 2-methyl, 3-methyl, 4-methyl, 2-methoxy, 3-methoxy, 4-methoxy, 4-fluoro, 2-chloro, 3-chloro, 4-chloro, 2,5-dichloro, 2,6-dichloro, 3,4-dichloro, 2-bromo, 2-methoxycarbonyl, 4-carboxy, 4-carboxymethyl, 4-ethoxycarbonylmethyl, 4-nitro and 4-(N,N-diethylaminosulfonyl)group.] or an acid addition salt thereof.

In the group of compounds described in the general formula (IA), there are some compounds contained in each invention described in the above item [PRIOR ART] as the broad scope, but there is no specific description about individual compound. Accordingly, all compounds represented by the general formula (IA) are considered to be quite novel.

Further, the present invention relates to the novel use as elastase inhibitors containing derivatives of p-guanidinobenzoic acid, as active ingredient, represented by the general formula:

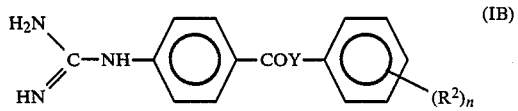

[wherein Y represents an oxygen atom or a sulfur atom and when Y is an oxygen atom, $R^2$ represents
  (i) a hydrogen atom,
  (ii) a alkyl group of one to four carbon atoms,
  (iii) an alkoxy group of one to four carbon atoms, (iv) an alkoxymethyl group of two to five carbon atoms, (v) a group represented by the formula: COOR$^3$ (wherein R$^3$ represents a hydrogen atom or an alkyl group of one to four carbon atoms.), (vi) a group represented by the formula: CH$_2$COOR$^3$ (wherein R$^3$ is the same meaning as described hereinbefore.), (vii) a group represented by the general formula: CH=CH—COOR$^3$ (wherein R$^3$ is the same meaning as described hereinbefore.), (viii) a halogen atom, (ix) a trifluoromethyl group, (x) a group represented by the formula: COR$^4$ (wherein R$^4$ represents an alkyl group of one to four carbon atoms, a phenyl group, guanidinophenyl group, cyclopentylmethyl group or cyclohexylmethyl group.), (xi) a group represented by the formula: OCOR$^4$ (wherein R$^4$ is the same meaning as described hereinbefore.), (xii) a group represented by the general formula: CH$_2$OCOR$^4$ (wherein R$^4$ is the same meaning as described hereinbefore.), (xiii) a group represented by the general formula: SO$_2$R$^4$ (wherein R$^4$ is the same meaning as described hereinbefore.), (xiv) a group represented by the general formula: OSO$_2$R$^4$ (wherein R$^4$ is the same meaning as described hereinbefore.), (xv) a group represented by the general formula: CONR$^5$R$^6$ (wherein R$^5$ and R$^6$ represent a hydrogen atom, an alkyl group of from one to four carbon atoms, a phenyl group, a benzyl group, a pyridyl group independently, or R$^5$, R$^6$ and a nitrogen atom, to which R$^5$ and R$^6$ are linked, together represent a pyrrolidinyl group, a piperidino group or morpholino group.), (xvi) a group represented by the general formula: OCONR$^5$R$^6$ (wherein R$^5$ and R$^6$ are the same meaning as described hereinbefore.), (xvii) a group represented by the general formula: SO$_2$NR$^5$R$^6$ (wherein R$^5$ and R$^6$ are the same meaning as described hereinbefore.), (xviii) a group represented by the general formula:

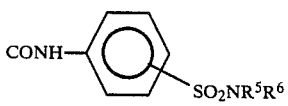

(wherein R$^5$ and R$^6$ are the same meaning as described hereinbefore.), (xix) a group represented by the general formula: NHSO$_2$R$^7$ (wherein R$^7$ represents an alkyl group of from one to four carbon atoms or a phenyl group.), (xx) a nitro group, (xxi) a hydroxy group, (xxii) a hydroxymethyl group, (xxiii) a guanidino group, (xxiv) a benzyloxy group, (xxv) a guanidinophenylthiomethyl group, (xxvi) a morpholinosulfonylphenoxymethyl, (xxvii) a pyridyloxymethyl or (xxviii) (1,1-dioxothiazol-3-yl)carbonyl group.

(ii) when Y is a sulfur atom, R$^2$ represents (i) a hydrogen atom, (ii) an alkyl group of one to four carbon atoms, (iii) an alkoxy group of one to four carbon atoms, (iv) a halogen atom, (v) a group represented by the formula: COOR$^3$ (wherein R$^3$ is the same meaning as described hereinbefore.), (vi) a group represented by the formula: CH$_2$COOR$^3$ (wherein R$^3$ is the same meaning as described hereinbefore.), (vii) a nitro group or (viii) a group represented by the general formula: SO$_2$NR$^5$R$^6$ (wherein R$^5$ and R$^6$ are the same meaning as described hereinbefore.)

and symbol n represents an integer of one to five, and when symbol n represents more than two, each of R$^2$ may be the same group or the different group.] or an acid addition salt thereof.

In this specification containing claims, the term "an alkyl group" means the straight- or branched-chained alkyl group.

In the general formula (IB), as the alkyl group represented by R$^2$, as the alkyl moiety in the alkoxy group represented by R$^2$ and as the alkyl group represented by R$^3$, R$^4$, R$^5$, R$^6$ and R$^7$, a methyl, an ethyl, a propyl, a butyl group and the isomer thereof are cited, and all of them are preferred.

In the general formula (IB), as the halogen atom represented by R$^2$, a fluorine atom, a chlorine atom, a bromine atom and an iodine atom are cited, and all of them are preferred.

In the general formula (IB), as the group represented by R$^2$, and all group represented by (i) to (xxvii) is preferred.

The acid addition salts of the compounds represented by the general formula (IA) and (IB) are preferably non-toxic and water-soluble.

Suitable acid addition salts include, for example, an inorganic acid addition salt such as hydrochloride, hydrobromide, hydroiodide, sulfate, phosphate, nitrate, or an organic acid addition salt such as acetate, lactate, tartrate, benzoate, citrate, methanesulfonate, ethanesulfonate, benzenesulfonate, toluenesulfonate, isethionate, glucuronate, gluconate.

All compounds of the present invention, represented by the general formula (IB) [including the compounds represented by the general formula (IA)] may be prepared by well-known methods.

For example, it may be prepared by reacting an acid addition salt of a compounds represented by the general formula:

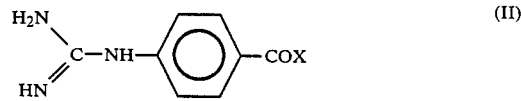

(wherein X represents an halogen atom)

with a compounds represented by the general formula:

(wherein Y, R$^2$ and n are the same meaning as described hereinbefore).

As the above reaction is the condensation accompanied by the formation of hydrogen halide, it is advantageous to use a dehydrohalogenation agent to promote the reaction.

As for the dehydrohalogenation agent, there can be used a tertiary organic amine, or if desired, there can be used a inorganic base such as a metal bicarbonate, etc.

As a tertiary organic amine, there can be used aliphatic, aromatic or heterocyclic amine, for example, triethylamine, tributylamine, dimethylaniline, pyridine and the like.

Particularly, pyridine is preferable because it is useful also as a solvent of reaction ingredient.

Further, as an inorganic base, there can be used, for example, sodium bicarbonate, sodium carbonate, sodium hydroxide and the like.

As a solvent there can be used, for example, benzene, toluene, tetrahydrofuran, pyridine and the like, and as described above, pyridine acts also as a dehydrohalogenation agent and is, therefore, particularly preferable.

Since the reaction proceeds comparatively fast, it may be carried out at the room temperature, or if desired, with a little cooling, generally the reaction may be carried out at a temperature from 0° C. to the room temperature.

The reaction time varies depending upon the reaction temperature to be used, and it is generally 30 minutes to 4 hours, preferably 30 minutes to 2.5 hours.

In carrying out the reaction, the starting material (III) described above is dissolved in a solvent, preferably in pyridine, the starting materials (II) is added into above solution.

When pyridine is used as a solvent, the compound (II) is not dissolved therein and therefore the reaction is hetetogeneous system. However the desired product is soluble in pyridine, and therefore the reaction mixture becomes homogeneous with the progress of the reaction. In the case where any other solvent than pyridine is used, the reaction mixture is not always homogeneous but the reaction can be carried out in a heterogeneous system.

The desired product is obtained as a salt with hydrogen halide. The product may be separated and purified by the following post-treatment. That is to say, the reaction mixture is concentrated or not concentrated depending upon the used solvent. If not concentrated, the product is crystallized as the carbonate salt by adding sodium bicarbonate to the reaction mixture. Particularly when pyridine is used as a solvent, the carbonate salt of the product is obtained as crystals by treating the reaction product mixture with sodium bicarbonate, without evaporation and concentration. Of course, it is possible to obtain the product by the evaporation of the solvent, but it is preferable that the product is crystallized as a salt as mentioned above, because in the latter case the product is higher in purity than in the former treatment.

The compounds (IB) of the present invention thus obtained can be converted further, if desired, to a suitable acid addition salt described above by known methods.

Besides, in the case that the product is crystallized as no salt in the route of conversion to a salt mentioned above, the product can be purified by column chromatography using silica-gel, etc.

The starting materials (II), used in the above-mentioned reaction, can be prepared by the conventional method that p-guanidinobenzoic acid may be reacted with thionylchloride.

In this case, the starting materials (II) can be prepared as the salt with hydrogen halide, especially hydrochloride.

The starting materials (II) may be obtained as the salt with a hydrogen halide which is by-produced in the formation of acid halide (II) from guanidinobenzoic acid, and it is advantageous that the obtained salt may be used without any operation.

The compounds represented by the general formula (III) are known compounds, or can be prepared easily by the known methods.

Further, of the compound of the present invention represented by the general formula (IB), the compound wherein at least one group of $R^2$ represent a carboxyl group, that is, the compounds represented by the general formula:

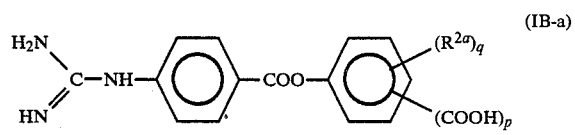

(IB-a)

(wherein $R^{2a}$ represents the groups hereinbefore described for $R^2$ except for a carboxy group, and p represents an integer of between one to five and q represents zero and an integer of between one to four, and the total number of p and q represented an integer of between one to five.)

can be obtained by subjecting the compounds represented by the general formula:

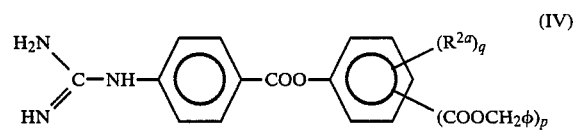

(IV)

(wherein symbol $\Phi$ represents a phenyl group and the other symbols are the same meaning as described hereinbefore) to the reaction for eliminating benzyl group. The said reaction for eliminating benzyl group may be carried out, for example, using anhydrous solution of hydrogen bromide-acetic acid in an atmosphere of an inert gas (e.g. argon, nitrogen etc.).

It is suitable that the reaction temperature is generally at 0° to 50° C., preferably at the room temperature.

And the compound (IV) can be obtained by subjecting the acid addition salt of the compounds represented by the general formula (II) and the compounds represented by the general formula:

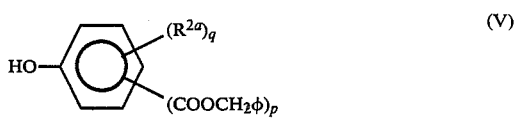

(V)

(wherein all symbols are the same meaning as described hereinbefore.) to esterification reaction.

This reaction may be carried out by the same conditions as mentioned hereinbefore.

And the compound (V) can be obtained by subjecting the compounds represented by the general formula:

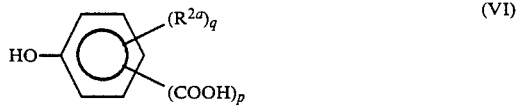

(wherein all symbols are the same meaning as described hereinbefore.) to benzylation reaction.

The benzylation reaction may be carried out by the known methods.

The compound represented by the general formula (VI) is the known compound or can be easily prepared by the known methods.

In the compound of present invention represented by the general formula (IB), the compound wherein at least one group of $R^2$ represents a hydroxymethyl group, i.e., the compound represented by the general formula:

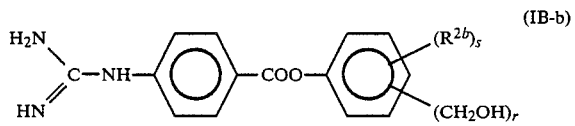

(wherein $R^{2b}$ represents the groups hereinbefore described for $R^2$ except for a hydroxymethyl group, and r represents an integer of between one to five and s represents zero and an integer of between one to four, and the total number of r and s represented an integer of between one to five, the other symbols are the same meaning as described hereinbefore.) can be obtained by subjecting the compounds represented by the general formula:

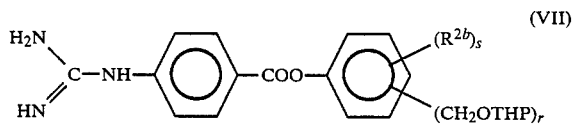

(wherein THP represents 2-tetrahydropyranyl group and the other symbols are the same meaning as described hereinbefore.) to reaction for eliminating a THP group.

The said reaction for eliminating a THP group may be carried in an aqueous solution of an organic acid such as acetic acid, propionic acid, oxalic acid, p-toluenesulfonic acid (preferably, acetic acid), or in an aqueous solution of an inorganic acid such as hydrochloric acid and sulfuric acid. Suitably, it may be carried out in the presence of a water-miscible organic solvent, for example, methanol, or an ether such as 1,2-dimethoxyethane, dioxane or tetrahydrofuran, at a temperature of ambient to 75° C. (preferably more than 37° C.).

And the compound (VII) may be obtained by subjecting an acid addition salt of the compound represented by the general formula (II) and the compounds represented by the general formula:

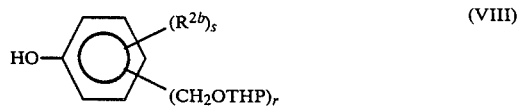

(wherein all symbols are the same meaning as described hereinbefore.) to esterification reaction.

The said reaction may be carried out by the same conditions as mentioned above.

The compound represented by the formula (VIII) can be obtained by subjecting the compounds represented by the general formula:

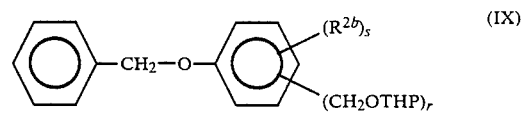

(wherein all symbols are the same meaning as described hereinbefore.) to the reaction for eliminating a benzyl group.

The said reaction for eliminating benzyl group may be carried out, for example, in an atmosphere of hydrogen gas, using palladium-carbon as catalyst in ethyl acetate, ethanol or benzene etc., at a temperature of 0° C. to 40° C., preferably ambient.

The compounds represented the formula (IX) are known compounds or can be obtained by the known methods.

Further, of the compounds of the present invention represented by the general formula (IB), those represented by the general formula:

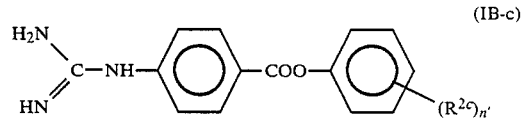

[wherein $R^{2c}$ represents
  (i) a hydrogen atom,
  (ii) an alkyl group of one to four carbon atoms,
  (iii) an alkoxy group of one to four carbon atoms,
  (iv) an alkoxymethyl group of two to five carbon atoms,
  (v) a group represented by the formula: $COOR^3$ (wherein $R^3$ represents a hydrogen atom or an alkyl group of one to four carbon atoms.),
  (vi) a group represented by the formula: $CH_2COOR^3$ wherein $R^3$ is the same meaning as described hereinbefore.),
  (vii) a halogen atom,
  (viii) a trifluoromethyl group,
  (ix) a group represented by the general formula: $COR^4$ (wherein $R^4$ represents an alkyl group of from one to four carbon atoms, a phenyl group, guanidinophenyl group, cyclopentylmethyl group or cyclohexylmethyl group.),
  (x) a group represented by the formula: $OCOR^4$ (wherein $R^4$ is the same meaning as described hereinbefore.),
  (xi) a group represented by the general formula: $CH_2OCOR^4$ (wherein $R^4$ is the same meaning as described hereinbefore.),
  (xii) a group represented by the general formula: $SO_2R^4$ (wherein $R^4$ is the same meaning as described hereinbefore.),
  (xiii) a group represented by the general formula: $OSO_2R^4$ (wherein $R^4$ is the same meaning as described hereinbefore.),
  (xiv) a group represented by the general formula: $CONR^5R^6$ (wherein $R^5$ and $R^6$ represent a hydrogen atom an alkyl group of from one to four carbon atoms, a phenyl group, a benzyl group, pyridyl group independently, or $R^5$, $R^6$ and a nitrogen atom, to which $R^5$ and $R^6$ are linked, together represent a pyrrolidinyl group, a piperidino group or morpholino group.), (xv) a group represented by the general formula: $OCONR^5R^6$ (wherein $R^5$ and $R^6$ are the same meaning as described hereinbefore.), (xvi) a group represented by the general formula: $SO_2NR^5R^6$ (wherein $R^5$ and $R^6$ are the same meaning as described hereinbefore.), (xvii) a group represented by the general formula:

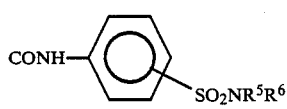

(wherein $R^5$ and $R^6$ are the same meaning as described hereinbefore.), (xviii) a group represented by the general formula: $NHSO_2R^7$ (wherein $R^7$ represents an alkyl group of from one to four carbon atoms or a phenyl group.), (xix) a hydroxy group, (xx) a guanidino group, (xxi) a benzyloxy group, (xxii) a guanidinophenylthiomethyl group, (xxiii) a morpholinosulfonylphenoxymethyl or (xxiv) a pyridyloxymethyl group and symbol n' represents an integer of one to five, and when symbol n' represents more than two, each of $R^{2c}$ represents the same group or the different group.] may be prepared by reacting the compounds described by the general formula:

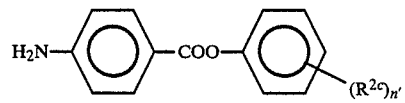

(wherein $R^{2c}$ and n' are the same meaning as described hereinbefore.)

with a cyanamide described by the formula:

$H_2N-CN$ (XI)

The above-mentioned reaction may be carried out bey adding the starting material (X) into water or an inert organic solvent such as methanol, ethanol, tetrahydrofuran, or into the mixed solvent of water and alcohol, adding thereto an excess amount of a compound of the formula (XI) under the existence of equimolecular or excess amount to the compound (X), of a mineral acid such as hydrochloric acid, sulfuric acid, and then reacting for 15 minutes to two hours at a temperature from ambient to the reflux temperature of the reaction mixture.

The desired compound prepared may be isolated and purified by the same method as hereinbefore described, and if required, converted into an acid addition salt thereof.

The starting material (X), used in above-mentioned reaction, may be easily prepared by dissolving the corresponding p-nitrobenzoic acid phenyl ester compound in a lower alkanol such as ethanol, and them subjecting to catalytic reduction in the presence of a hydrogenation catalyst such as palladium on charcoal, palladium black, platinum dioxide or nickel at atmospheric temperature and pressure or by heating and adding pressure.

The cyanamide (XI), another starting material, is a known compound.

EFFECT

Delivatives of p-guanidinobenzoic acid phenyl ester described by the general formula (IA) and (IB), and acid addition salts thereof, of the present invention, have an inhibitory effect on elastase. Accordingly, it is useful for treatment and/or prevention of diseases induced by the abnormal enhancing of the degradation of elastin, collagen fiber and/or proteoglican, by the action of elastase, in mammals, especially in human beings.

Examples of such diseases are pulmonary emphysema, atherosclerosis and rheumatoid arthritis and the like.

An inhibitory effects of compounds on elastase were confirmed by the screening system mentioned below.

INHIBITORY EFFECT ON ELASTASE (1) Method of Experiment

The test was carried out by the slight modification of the method of Bieth et al [see Biochem. Med., 75, 350 (1974)] using elastase from human neutrophil.

Namely, it is a spectrophotometric method using the synthesized substrate [succinyl-alanyl-prolyl-alanyl-p-nitroanilide (Suc-Ala-Pro-Ala-pNA, produced by peptide laboratory)] which has comparatively high specificity neutrophil elastase.

The reaction mixture consisted of 1 mM Suc-Ala-Pro-Ala-pNA (dissolving in N-methylpyrrolidone to the concentration of 100 mM, and then adding 1/100 amount of the solution to the reaction mixture.), 0.1 M buffer solution of tris-hydrochloric acid (pH 8.0), 0.2 M sodium chloride aqueous solution, the sample solution of various concentrations and enzyme solution in a final volume of 1.0 ml was incubated at 37° C. for 30 minutes.

The reaction was stopped by the addition of 100 μl of 50% acetic acid into the reaction mixture, and then p-nitro anilide released was measured on absorbance of 405 nm.

Inhibition percentage of the test compounds was caliculated by the following equation:

Inhibition % =

$$\left(1 - \frac{OD_{405\ nm}\ \text{count of sample} - \text{background}}{OD_{405\ nm}\ \text{count of control} - \text{background}}\right) \times 100$$

(2) Results

The results are shown in Table 1.

TABLE 1

Inhibitory Effect on Elastase

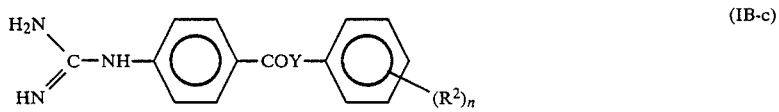

(IB-c)

(1) when Y represents an oxygen atom in the general formula (IB-c):

| Example No. | Structural Formula of Sample ($R^2$)n | Salt | Inhibition % at 100 μM | IC50 (μM) |
|---|---|---|---|---|
|  | hydrogen[1] | phosphate | 54.6[2] |  |
| 2 | 2-methyl | mesylate | 20.2 |  |
| 3 | 3-methyl | mesylate | 45.6 |  |
|  | 4-methyl[1] | mesylate | 28.4 |  |
| 4 | 2,3-dimethyl | mesylate | 5.9 |  |
| 5 | 3,5-dimethyl | mesylate | 46.2 |  |
| 6 | 3-ethyl | mesylate | 39.6 |  |
| 7 | 2-methoxy | mesylate | 23.1 |  |
| 8 | 3-methoxy | mesylate | 50.9 | 100 |
| 9 | 4-methoxy | mesylate | 44.4 |  |
| 10 | 3,5-dimethoxy | acetate |  | 40.0 |
| 11 | 5-etanesulfonyloxy-3-methoxymethyl | acetate | 66.0 | 60.0 |
| 12 | 3-hydroxy-5-methoxymethyl | acetate | 14.0 | >200 |
| 13 | 5-(4-guanidinobenzoyloxy)-3-methoxymethyl | 2 acetate | 89.0 | 9.1 |
| 148 | 3-carboxy-2-chloro | hydrobromide |  | 20.0 |
| 147 | 3,5-dicarboxy | hydrobromide | 25.0 |  |
| 149 | 2-carboxy-5-chloro | hydrobromide |  | 60.0 |
| 14 | 2-chloro-3-methoxycarbonyl | mesylate | 90.7 | 4.0 |
| 15 | 2-chloro-4-methoxycarbonyl | mesylate | 55.6 | 98.0 |
| 16 | 3-chloro-4-methoxycarbonyl | mesylate | 42.0 |  |
| 17 | 5-chloro-2-methoxycarbonyl | mesylate | 92.2 | 5.8 |
| 18 | 3-chloro-5-methoxycarbonyl | acetate |  | 1.8 |
| 19 | 3,5-bis(isopropoxycarbonyl) | mesylate | 5.2 |  |
| 20 | 5-chloro-2-isopropoxycarbonyl | mesylate |  | 14.0 |
| 21 | 2-chloro-3-isopropoxycarbonyl | mesylate |  | 2.0 |
| 22 | 3-sec-butoxycarbonyl-2-chloro | mesylate |  | 2.6 |
| 23 | 3-methoxycarbonylmethyl | acetate | 15.6 |  |
| 24 | 2-chloro-3-methoxycarbonylmethyl | mesylate |  | 50.0 |
| 25 | 2-chloro-4-methoxycarbonylmethyl | mesylate | 40.0 |  |
| 26 | 3-chloro-4-methoxycarbonylmethyl | mesylate | 13.3 |  |
| 27 | 4-(2-methoxycarbonylvinyl) | mesylate | 31.0 |  |
| 28 | 2-fluoro | mesylate | 76.3 | 40.0 |
| 29 | 3-fluoro | mesylate | 81.1 | 21.0 |
| 30 | 4-fluoro | mesylate | 10.7 |  |
| 31 | 2,6-difluoro | mesylate |  | 3.7 |
| 32 | 2,3-difluoro | acetate |  | 3.7 |
| 33 | 2,3,4,5,6-pentafluoro | mesylate | 92.1 | 5.8 |
| 34 | 2-chloro | mesylate | 76.8 | 27.0 |
| 35 | 3-chloro | mesylate | 87.6 | 8.0 |
| 36 | 4-chloro | mesylate | 14.9[2] |  |
| 37 | 2,5-dichloro | mesylate | 85.8 | 1.1 |
| 38 | 2,6-dichloro | mesylate | 89.9 | 2.0 |
| 1 | 3,5-dichloro | mesylate | 97.0 | 0.4 |
| 39 | 3-chloro-5-methoxy | mesylate | 91.1 | 2.4 |
| 40 | 4-chloro-3-methoxy | mesylate | 39.0 |  |
| 41 | 2-chloro-5-methoxy | acetate |  | 13.0 |
| 42 | 2-bromo | mesylate | 82.1 | 16.0 |
| 43 | 3-bromo | mesylate | 91.7 | 6.0 |
| 44 | 4-iodo | mesylate | 11.2 |  |
| 45 | 2-trifluoromethyl | mesylate | 72.4 | 23.0 |
| 46 | 3-trifluoromethyl | mesylate | 71.4 | 13.0 |
| 47 | 3,5-bistrifluoromethyl | mesylate |  | 3.2 |
| 48 | 3-acetyl | mesylate | 4.1 |  |
| 49 | 2-acetyl-5-methoxy | acetate |  | 40.0 |
| 50 | 2-acetyl-5-propoxy | mesylate |  | 54.0 |
| 51 | 2-acetyl-5-chloro | acetate |  | 1.8 |
| 52 | 5-chloro-2-propionyl | mesylate |  | 1.6 |
| 53 | 5-chloro-2-isobutyl | acetate |  | 6.5 |
| 54 | 3-benzoyl | mesylate |  | 92.0 |
| 55 | 4-benzoyl | mesylate | 33.3 |  |
| 56 | 4-benzoyl-2-chloro | mesylate | 57.1 | 48.0 |
| 57 | 4-benzoyl-2,3-dichloro | mesylate | 50.5 |  |
| 58 | 5-chloro-2-cyclopentylacetyl | acetate |  | 1.9 |
| 59 | 3-acetoxy | acetate | 25.7 |  |
| 60 | 4-acetoxy | mesylate | 27.8 |  |
| 61 | 5-acetoxy-3-chloro | acetate |  | 0.48 |
| 62 | 3-chloro-5-propionyloxy | acetate |  | 0.38 |
| 63 | 3-benzyloxy | mesylate | 78.3 | 11.0 |

TABLE 1-continued

Inhibitory Effect on Elastase $$\text{H}_2\text{N}-\overset{\text{HN}}{\underset{}{\text{C}}}-\text{NH}-\underset{}{\bigcirc}-\text{COY}-\underset{(R^2)_n}{\bigcirc} \quad \text{(IB-c)}$$

| No. | (R²)n | Salt | Inhibition % at 50 μg/ml | IC50 (μM) |
|---|---|---|---|---|
| 64 | 3-(4-guanidinobenzoyloxy) | acetate | | 15.0 |
| 65 | 3,5-bis(4-guanidinobenzoyloxy) | 3 mesylate | 38.0 | |
| 66 | 3-acetyl-5-(4-guanidinobenzoyloxy) | 2 acetate | | 72.0 |
| 67 | 5-(4-guanidinobenzoyloxy)-3-methoxycarbonyl | 2 acetate | | 70.0 |
| 68 | 3-chloro-5-(4-guanidinobenzoyloxy) | acetate | | 0.6 |
| 69 | 5-(4-guanidinobenzoyloxy)-3-methoxy | 2 acetate | | 1.6 |
| 70 | 5-(4-guanidinobenzoyloxy)-3-methyl | acetate | | 6.4 |
| 71 | 5-acetoxymethyl-3-chloro | acetate | | 3.0 |
| 72 | 4-mesyl | mesylate | | >100.0 |
| 73 | 5-mesyloxy-3-methoxy | acetate | | 4.7 |
| 74 | 3-chloro-5-mesyloxy | acetate | | 1.0 |
| 75 | 3-chloro-5-ethanesulfonyloxy | acetate | | 1.1 |
| 76 | 3-chloro-5-isopropanesulfonyloxy | acetate | | 1.1 |
| 77 | 5-benzenesulfonyloxy-3-chloro | acetate | | 0.8 |
| 78 | 5-etanesulfonyloxy-3-methyl | acetate | | 27.0 |
| 79 | 5-carbamoyl-3-chloro | acetate | | 5.2 |
| 80 | 3-(N,N—dimethylcarbamoyl) | mesylate | 30.0 | |
| 81 | 2-chloro-3-(N—methylcarbamoyl) | mesylate | | 6.0 |
| 82 | 3-(4-guanidinobenzoyloxy)-5-(N—methylcarbamoyl) | 2 acetate | 38.0 | |
| 83 | 3,5-bis(N—ethylcarbamoyl) | mesylate | 28.0 | |
| 84 | 3,5-bis(N—propylcarbamoyl) | mesylate | 36.0 | |
| 85 | 5-(N—benzylcarbamoyl)-3-(4-guanidinobenzoyloxy) | 2 acetate | 27.0 | |
| 86 | 3-chloro-5-{N—(3-pyridyl)carbamoyl} | 2 acetate | | 0.93 |
| 87 | 3-chloro-5-(N,N—dimethylcarbamoyloxy) | acetate | | 0.76 |
| 88 | 3-chloro-5-(N—ethylcarbamoyloxy) | mesylate | | 1.1 |
| 89 | 3-sulfamoyl | acetate | | 65.0 |
| 90 | 3-chloro-4-(N,N—dimethylsulfamoyl) | acetate | | 140.0 |
| 91 | 2-(N,N—diethylsulfamoyl) | mesylate | | 180.0 |
| 92 | 3-(N,N—diethylsulfamoyl) | mesylate | | 35.0 |
| 93 | 4-(N,N—diethylsulfamoyl) | mesylate | | 58.0 |
| 94 | 3-chloro-4-(N,N—diethylsulfamoyl) | acetate | | 22.0 |
| 95 | 3-chloro-5-(N,N—diethylsulfamoyl) | acetate | | 4.8 |
| 96 | 4-(N,N—diethylsulfamoyl)-2-fluoro | acetate | | 61.0 |
| 97 | 4-(N,N—dipropylsulfamoyl) | mesylate | | 58.0 |
| 98 | 4-(1-pirolidinylsulfonyl) | acetate | | 77.0 |
| 99 | 3-piperidinosulfonyl | acetate | 41.0 | |
| 100 | 3-morpholinosulfonyl | acetate | 44.2 | |
| 101 | 4-morpholinosulfonyl | acetate | 34.9 | |
| 102 | 3-chloro-5-{N—(4-sulfamoylphenyl)carbamoyl} | acetate | | 1.3 |
| 103 | 3-chloro-5-[N—{4-(N,N—dimethylsulfamoyl)phenyl}carbamoyl | acetate | | 0.95 |
| 104 | 3-chloro-5-[N—{4-(N,N—diethylsulfamoyl)phenyl}carbamoyl | acetate | | 1.1 |
| 105 | 2-chloro-5-(N—mesylamino) | acetate | | 8.5 |
| 106 | 3-chloro-5-(N—ethanesulfonylamino | acetate | | 15.0 |
| 107 | 3-nitro | mesylate | 87.0 | 11.0 |
| 108 | 4-nitro | mesylate | 60.1 | 120.0 |
| 109 | 3-hydroxy-5-methyl | acetate | | 160.0 |
| 110 | 5-hydroxy-3-methoxy | acetate | | 20.0 |
| 111 | 5-hydroxy-3-methoxycarbonyl | acetate | 45.0 | |
| 112 | 3-chloro-5-hydroxy | mesylate | | 8.3 |
| 113 | 3-(4-guanidinobezoyloxy)-5-hydroxy | 2 mesylate | 42.0 | |
| 114 | 5-hydroxy-3-(N—methylcarbamoyl) | acetate | 22.0 | |
| 115 | 3-(N—benzylcarbamoyl)-5-hydroxy | acetate | | 88.0 |
| 150 | 3-chloro-5-hydroxymethyl | acetate | | 4.5 |
| 116 | 3-guanidino | 2 acetate | 20.0 | |
| 117 | 4-guanidino | 2 mesylate | | >100.0 |
| 118 | 2-chloro-5-guanidino | 2 acetate | | 47.0 |
| 119 | 5-benzyloxy-3-chloro | acetate | | 4.7 |
| 120 | 3-chloro-5-(4-guanidinophenylthiomethyl) | 2 acetate | | 6.0 |
| 151 | 3-chloro-5-morpholinosulfonylphenoxymethyl | acetate | | 1.4 |
| 152 | 3-methoxy-5-(4-morpholinosulfonyl)phenoxymethyl | acetate | | 7.0 |
| 121 | 3-chloro-5-(3-pyridyl)oxymethyl | 2 acetate | | 1.1 |
| 122 | 3-methoxy-5-(3'-sulfonylpyrrolidine)carboxamido | acetate | | 12.0 |
| 123 | 3-chloro-5-(3'-sulfonylpyrrolidinecarboxamido | acetate | | 3.1 |

(ii) when Y represents a sulfur atom in the general formula (IB-c)

| Example No. | Structural Formula of Sample (R²)n | Salt | Inhibition % at 50 μg/ml | IC50 (μM) |
|---|---|---|---|---|
| 124 | hydrogen | Phosphate | 94.0 | 2.1 |
| 125 | 2-methyl | mesylate | 76.3 | 20 |
| 126 | 3-methyl | mesylate | 89.7 | 5.0 |
| 127 | 4-methyl | tosylate | 29.3 | |
| 128 | 2-methoxy | mesylate | 79.8 | 21.0 |

TABLE 1-continued

Inhibitory Effect on Elastase

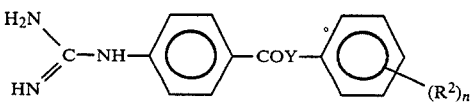
(IB-c)

| | | | | |
|---|---|---|---|---|
| 129 | 3-methoxy | sulfonate | 89.2 | 6.4 |
| 130 | 4-methoxy | mesylate | 48.2 | |
| 131 | 4-fluoro | mesylate | 83.0 | 21.0 |
| 132 | 2-chloro | mesylate | 93.0 | 1.8 |
| 133 | 3-chloro | mesylate | 81.2 | 0.3 |
| 134 | 4-chloro | mesylate | 69.5 | |
| 135 | 2,5-dichloro | mesylate | 92.1 | 0.1 |
| 136 | 2,6-dichloro | mesylate | 64.5 | 45 |
| 137 | 3,4-dichloro | mesylate | 35.5 | |
| 138 | 2-bromo | mesylate | 83.1 | 1.6 |
| 139 | 4-carboxyl | mesylate | 23.2 | |
| 140 | 4-carboxymethyl | sulfonate | 47.8 | |
| 141 | 2-methoxycarbonyl | mesylate | 96.3 | 2.6 |
| 142 | 4-ethoxycarbonyl | mesylate | 69.1 | |
| 144 | 4-ethoxycarboxymethyl | mesylate | 75.5 | |
| 145 | 4-nitro | mesylate | 64.2 | 18.0 |
| 146 | 4-(N,N—acethylaminosulfonyl) | acetate | 73.1 | 11.0 |

Remarks:
[1] shows that this compound is described in Example 4 in the specification of Japanese Patent Kokai No. 50-4038.
[2] shows inhibition percentage when the concentration of drug is 50 μg/ml.

The results of the experiment showed that the compounds of the present invention have an inhibitory effect on elastase.

Further, it was confirmed that the toxicity of the compounds of the present invention is enough low and they can be useful enough safely for medical supplies.

For example, in the acute toxicity test in mice by intravenous administration, the $LD_{50}$ values of compounds wherein Y represents an oxygen atom in the general formula (IB) and $(R^2)n$ represents 2,5-dichloro, a hydrogen atom, 3-chloro-5-hydroxy, 3-chloro-5-ethanesulfonyloxy and 3-chloro-4-(N,N-diethylsulfamoyl), were between 50 and 150 mg/kg, respectively.

The other the $LD_{50}$ values of compounds wherein Y represents a sulfur atom in the general formula (IB) and $(R^2)n$ represents 2,5-dichloro group, a hydrogen atom, 3-chloro-5-hydroxy, 3-chloro-5-ethanesulfonyloxy and 3-chloro-4-(N,N-diethylsulfamoyl), were between 50 and 150 mg/kg, respectively.

Accordingly, it was confirmed that the compounds of the present invention can be useful for the treatment and/or prevention of diseases induced by abnormal enhancing of degradation of proteins such as elastin and the like, by the action of elastase in mammals, especially in human beings.

For the purpose mentioned above, the compounds of the present invention, described in the general formula (IA) and (IB) or an acid addition salts thereof may normally be administered systemically or partially, usually by oral or parenteral administration.

The dose to be administered is determined depending upon age, body weight, symptom, the desired therapeutic effect, the route of administration, and the duration of the treatment etc. In the human adult, the doses per person for one time are generally between 50 mg and 500 mg, by oral administration up to several times per day, and between 10 mg and 200 mg, by parenteral administration (preferably by intravenous administration) up to several times per day.

As mentioned above, the doses to be used depend on various conditions. Therefore, there are cases in which doses lower than the ranges specified above and doses greater than the ranges specified above, may be used.

Solid compositions according to the present invention for oral administration include compressed tablets, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinyl-pyrrolidone or magnesium metasilicate aluminate. The compositions may also comprise, as is normal practice, additional substances other than inert diluents e.g. lubricating agents such as magnesium stearate, and, disintegrating agents such as cellulose calcium gluconate, stabilizing agents such as lactose, and solubilizers such as glutamic acid and asparaginic acid. The tablets or pills may, if desired, be made into gastric film-coated or enteric film-coated tablets or pills, such as sugar-coated, gelatin-coated, hydroxypropylcellulose-coated or hydroxypropylmethylcellulose phthalate-coated tablets or pills; two or more layers may be used. The compositions for oral administration also include capsules of absorbable material such as gelatin.

Liquid composition for oral administration include pharamceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other composition for oral administration include spray compositions which may be prepared by known methods and which comprise one or more of the active compound(s). Besides inert diluents such compositions may also comprise stabilizers such as sodium bisulfite and buffer for isotonicity, for example sodium chloride, sodium citrate or citric acid.

The manufacturing methods of spray compositions have been described in detail, for example, specifications of the U.S. Pat. Nos. 2868691 and 3095355.

Preparations for injection according to the present invention for parenteral administration include sterile aqueous or non-aqueous solutions, suspensions or emulsions. Example of aqueous solvents or suspending media are distilled water for injection and physiological salt solution. Examples of non-aqueous solvents or suspending media are propylene glycol, polyethylene glycol, vegetable oils such as olive oil, alcohols such as ethanol, Polysorbate 80 (registered Trade Mark). These compositions may also include adjuvants such as preserving, wetting, emulsifying and dispersing agents stabilizing agents (e.g. lactose) and solubilizers (e.g. glutamic acid and asparaginic acid). They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

EXAMPLE

The following Reference Examples and Examples illustrate the preparation of compounds of the present invention, however, the present invention is not restricted to them. In the Examples, "IR" represents "Infrared absorption spectrum". Except when specified otherwise, infrared absorption spectra were recorded by KBr tablet. In the table, "Mesylate" represents "methansulfonyl group".

EXAMPLE 1 p-guanidinobenzoic acid 3,5-dichlorophenyl ester methanesulfonate

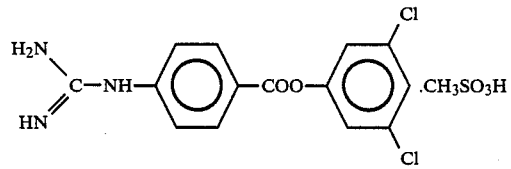

The mixture of 700 mg of p-guanidinobenzoyl chloride hydrochloride (prepared by the methods described in Example 1 of each of the specification of Japanese Patent Kokai No. 55-115865 and U.S. Pat. No. 4283418), 490 mg of 3,5-dichlorophenol and 10 ml of pyridine was stirred for thirty minutes. Diethyl ether was added into the reaction mixture, and the mixture was decanted.

A saturated aqueous solution of sodium bicarbonate was added into the obtained layer of ether to obtain the desired carbonate.

The obtained crystal was washed with water and acetone, successive, was dried in vacuum.

Dried crystal was suspended in ethanol, 0.124 ml of methanesulfonic acid was added thereto, and precipitated crystal was dried in vacuum to give 506 mg of the title compound (white crystal) having the following physical data:

Melting Point: 232°–234° C.

IR Value: $\nu$ 3340, 3150, 1730, 1680, 1620, 1600, 1570, 1550, 1410, 1260, 1200, 1170, 1090, 1060, 1040 cm$^{-1}$.

Hereinafter, by the same procedure as described in Example 1, p-guanidinobenzoyl chloride hydrochloride and desired phenol compound or thiophenol compounds were used to obtain compounds of the present invention described in following table 2 [compound (IB) wherein Y is an oxygen atom) and table 3 [compounds (IB) wherein Y is a sulfur atom].

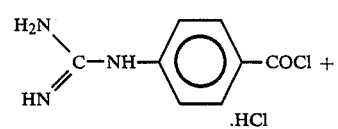

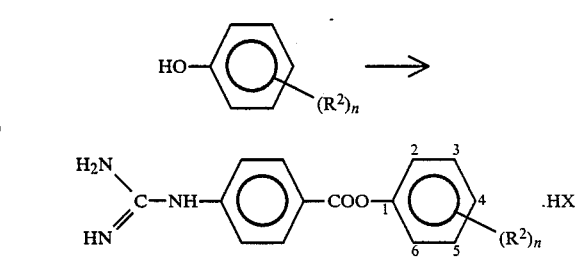

TABLE 2

| Example No. | The Structure of Products (R$^2$)n | HX (Salt) | The Appearance of Products | m.p. and IR Value of Products |
|---|---|---|---|---|
| 1 | hydrogen | phosphate | white crystal | 205~208° C. |
| 2 | 2-methyl | mesylate | yellow crystal | 199~200° C. |
| 3 | 3-methyl | mesylate | white powder | 143~144° C. |
| 4 | 2,3-dimethyl | mesylate | yellow crystal | 202~205° C. |
| 5 | 3,5-dimethyl | mesylate | pale yellow crystal | 184~185° C. |
| 6 | 3-ethyl | mesylate | white crystal | 142~143° C. |
| 7 | 2-methoxy | mesylate | white crystal | 196~197° C. |
| 8 | 3-methoxy | mesylate | white crystal | 162~164° C. |
| 9 | 4-methoxy | mesylate | pink crystal | 173~174° C. |
| 10 | 3,5-dimethoxy | acetate | yellow wax | $\nu$ 2900~3400, 1730, 1570~1610, 1470, 1420, 1260, 1130, 1070, 1040 cm$^{-1}$ (neat) |
| 11 | 5-etanesulfonyloxy-3-methoxymethyl | acetate | pale brown bubbly powder | $\nu$ 2500~3500, 1730, 1680, 1570, 1400, 1360, 1255, 1170, 1110, 1070 cm$^{-1}$ |
| 12 | 3-hydroxy-5-methoxymethyl | acetate | creamy colored bubbly powder | $\nu$ 3700~3300, 3300~2300, 1720, 1685, 1600, 1570, 1450, 1410, 1265, 1135, 1080 cm$^{-1}$ |
| 13 | 5-(4-guanidinobenzoyloxy)-3- | 2 acetate | brown bubbly powder | $\nu$ 3700~2250, 1740, 1690, 1560, |

TABLE 2-continued

| Example No. | The Structure of Products (R²)n | HX (Salt) | The Appearance of Products | m.p. and IR Value of Products |
|---|---|---|---|---|
|  | methoxymethyl |  |  | 1400, 1260, 1180, 1125, 1070 cm$^{-1}$ |
| 14 | 2-chloro-3-methoxycarbonyl | mesylate | white powder | 188~190° C. |
| 15 | 2-chloro-4-methoxycarbonyl | mesylate | white powder | 206~207° C. |
| 16 | 3-chloro-4-methoxycarbonyl | mesylate | pink powder | 206~210° C. |
| 17 | 5-chloro-2-methoxycarbonyl | mesylate | white powder | 170~175° C. |
| 18 | 3-chloro-5-methoxycarbonyl | acetate | white bubbly powder | ν 3480, 3000, 1730, 1600, 1640, 1580, 1420, 1260, 1170, 1100, 1060 cm$^{-1}$ |
| 19 | 3,5-bis(isopropoxycarbonyl) | mesylate | white crystal | 155~157° C. |
| 20 | 5-chloro-2-isopropoxycarbonyl | mesylate | white crystal | 202~203° C. |
| 21 | 2-chloro-3-isopropoxycarbonyl | mesylate | white bubbly powder | ν 3300, 3150, 1720, 1680, 1600, 1570, 1240, 1040 cm$^{-1}$ |
| 22 | 3-sec-butoxycarbonyl-2-chloro | mesylate | white crystal | 177~180° C. |
| 23 | 3-methoxycarbonylmethyl | acetate | colorless oil | ν 3500~3300, 1700~1500, 1400 cm$^{-1}$ (neat) |
| 24 | 2-chloro-3-methoxycarbonylmethyl | mesylate | white crystal | 194~196° C. |
| 25 | 2-chloro-4-methoxycarbonylmethyl | mesylate | white powder | 170~171° C. |
| 26 | 3-chloro-4-methoxycarbonylmethyl | mesylate | white powder | 181~182° C. |
| 27 | 4-(2-methoxycarbonylvinyl) | mesylate | pink crystal | 225~230° C. |
| 28 | 2-fluoro | mesylate | pink crystal | 168~170° C. |
| 29 | 3-fluoro | mesylate | white crystal | 97~101° C. |
| 30 | 4-fluoro | mesylate | white crystal | 163~164° C. |
| 31 | 2,6-difluoro | mesylate | white powder | 219~221° C. |
| 32 | 2,3-difluoro | acetate | white crystal | >300° C. |
| 33 | 2,3,4,5,6-pentafluoro | mesylate | white crystal | 181~183° C. |
| 34 | 2-chloro | mesylate | pale orange crystal | 198~200° C. |
| 35 | 3-chloro | mesylate | white crystal | 200~202° C. |
| 36 | 4-chloro | mesylate | white crystal | 185~188° C. |
| 37 | 2,5-dichloro | mesylate | white crystal | 221~223° C. |
| 38 | 2,6-dichloro | mesylate | pink crystal | 234~237° C. |
| 39 | 3-chloro-5-methoxy | mesylate | white powder | 205~207° C. |
| 40 | 4-chloro-3-methoxy | mesylate | white powder | 125~128° C. |
| 41 | 2-chloro-5-methoxy | acetate | white bubbly powder | ν 3360, 3000, 1745, 1680, 1600, 1570, 1500, 1410, 1260, 1160, 1080, 1020 cm$^{-1}$ |
| 42 | 2-bromo | mesylate | pale pink crystal | 194~197° C. |
| 43 | 3-bromo | mesylate | white crystal | 212~214° C. |
| 44 | 4-iodo | mesylate | white crystal | 174~176° C. |
| 45 | 2-trifluoromethyl | mesylate | white crystal | 191~193° C. |
| 46 | 3-trifluoromethyl | mesylate | white crystal | 195~198° C. |
| 47 | 3,5-bistrifluoromethyl | mesylate | yellow powder | 194~198° C. |
| 48 | 3-acetyl | mesylate | white crystal | 180~182° C. |
| 49 | 2-acetyl-5-methoxy | acetate | brown wax | ν 2900~3500, 1730, 1680, 1480, 1260, 1140 cm$^{-1}$ (neat) |
| 50 | 2-acetyl-5-propoxy | mesylate | brown oil | ν 3300, 3150, 1740, 1670, 1600, 1560, 1060, 1040 cm$^{-1}$ (neat) |
| 51 | 2-acetyl-5-chloro | acetate | brown bubbly powder | ν 3400, 3000, 1740, 1690, 1600, 1570, 1400, 1260, 1180, 1060 cm$^{-1}$ |
| 52 | 5-chloro-2-propionyl | mesylate | white bubbly powder | ν 3400, 3000, 1740, 1690, 1590, 1440, 1410, 1370, 1250, 1180, 1120, 1070 cm$^{-1}$ |
| 53 | 5-chloro-2-isobutyryl | acetate | yellow bubbly powder | ν 3350, 3000, 1735, 1680, 1580, 1400, 1260, 1200, 1170, 1080, 1060, 1010 cm$^{-1}$ |
| 54 | 3-benzoyl | mesylate | white powder | 172~175° C. |
| 55 | 4-benzoyl | mesylate | brown powder | 218~220° C. |
| 56 | 4-benzoyl-2-chloro | mesylate | white powder | 190~192° C. |
| 57 | 4-benzoyl-2,3-dichloro | mesylate | white powder | 169~173° C. |
| 58 | 5-chloro-2-cyclopentylacetyl | acetate | white bubbly powder | ν 3350, 2950, 1540, 1690, 1600, 1570, 1400, 1260, 1200, 1180, 1060 cm$^{-1}$ |
| 59 | 3-acetoxy | acetate | brown wax | ν 3350, 3150, 1720, 1680, 1610, 1580, 1410, 1270, 1140, 1080, 1050 cm$^{-1}$ (neat) |
| 60 | 4-acetoxy | mesylate | pale brown wax | ν 3650~2500, 1760, 1740, 1700, 1680, 1630, 1610, 1570, 1510, 1470, 1410, 1375, 1280 cm$^{-1}$ |
| 61 | 5-acetoxy-3-chloro | acetate | white bubbly powder | ν 3400, 3100, 1740, 1685, 1600, 1400, 1320, 1260, 1140, 1070, 1010 cm$^{-1}$ |
| 62 | 3-chloro-5-propionyloxy | acetate | pale brown amorphous | ν 2500~3500, 1720, 1680, 1580, 1400 cm$^{-1}$ |
| 63 | 3-benzoyloxy | mesylate | pale brown wax | ν 3200, 1730, 1680, 1600, 1570, 1480, 1450, 1410, 1250, 1130 cm$^{-1}$ (neat) |
| 64 | 3-(4-guanidinobenzoyloxy) | acetate | white bubbly powder | ν 3350, 3150, 1730, 1680, 1600, 1570, 1250, 1170, 1130, 1060, 1040, 1020 cm$^{-1}$ |

TABLE 2-continued

| Example No. | The Structure of Products (R²)n | HX (Salt) | The Appearance of Products | m.p. and IR Value of Products |
|---|---|---|---|---|
| 65 | 3,5-bis(4-guanidinobenzoyloxy) | 3 mesylate | pale yellow bubbly powder | ν 3350, 3150, 1730, 1680, 1600, 1560, 1450, 1250, 1170, 1120, 1060, 1040 cm$^{-1}$ |
| 66 | 3-acetyl-5-(4-guanidinobenzoyloxy) | 2 acetate | while solid | ν 3650~2200, 1740, 1690, 1570, 1410, 1260, 1180, 1135, 1070 cm$^{-1}$ |
| 67 | 5-(4-guanidinobenzoyloxy)-3-methoxycarbonyl | 2 acetate | pale brown solid | ν 3650~2300, 1730, 1690, 1570, 1400, 1260 cm$^{-1}$ |
| 68 | 3-chloro-5-(4-guanidinobenzoyloxy) | acetate | yellow bubbly powder | ν 3150, 1740, 1680, 1600, 1560, 1440, 1270, 1180, 1130, 1060, 1040 cm$^{-}$ |
| 69 | 5-(4-guanidinobenzoyloxy)-3-methoxy | 2 acetate | colorless solid | ν 3650~2200, 1740, 1690, 1610, 1570, 1410, 1260, 1180, 1150, 1130, 1070, 1020 cm$^{-1}$ |
| 70 | 5-(4-guanidinobenzoyloxy)-3-methyl | 2 acetate | pale brown bubbly powder | ν 2500~3600, 1720, 1680, 1560, 1400, 1260, 1175, 1120, 1070 cm$^{-1}$ |
| 71 | 5-acetoxymethyl-3-chloro | acetate | colorless oil | ν 3400, 1730, 1680, 1560, 1400, 1240, 1170, 1140, 1060, 1010, 860, 740, 640 cm$^{-1}$ |
| 72 | 4-mesyl | mesylate | white powder | 200~215° C. |
| 73 | 5-mesyloxy-3-methoxy | acetate | white bubbly powder | ν 3400, 1730, 1680, 1600, 1400, 1360, 1260, 1180, 1140, 1110, 1060 cm$^{-1}$ |
| 74 | 3-chloro-5-mesyloxy | acetate | white bubbly powder | ν 3400, 3000, 1740, 1690, 1600, 1440, 1410, 1370, 1250, 1180, 1120, 1070 cm$^{-1}$ |
| 75 | 3-chloro-5-ethanesulfonyloxy | acetate | white bubbly powder | ν 3350, 3000, 1740, 1680, 1590, 1560, 1400, 1260, 1200, 1180, 1060, 1020 cm$^{-1}$ |
| 76 | 3-chloro-5-isopropanesulfonyloxy | acetate | white bubbly powder | ν 3400, 2900, 1740, 1640, 1600, 1430, 1400, 1240, 1180, 1110, 1060 cm$^{-1}$ |
| 77 | 5-benzenesulfonyloxy-3-chloro | acetate | white bubbly powder | 190~195° C. |
| 78 | 5-etanesulfonyloxy-3-methyl | acetate | pale brown bubbly powder | ν 2500~3600, 1730, 1680, 1560, 1400, 1260, 1170, 1110 cm$^{-1}$ |
| 79 | 5-carbamoyl-3-chloro | acetate | white amorphous | ν 3400, 1680, 1570, 1400, 1300, 1270, 1230, 1180, 1100, 1080, 1010, 880, 850, 760, 650 cm$^{-1}$ |
| 80 | 3-(N,N—dimethyl)carbamoyl | mesylate | white solid (hygroscopicity) | ν 3650~3200, 3150, 1735, 1680, 1600, 1570, 1510, 1480, 1450, 1400, 1310, 1280, 1200, 1060 cm$^{-1}$ |
| 81 | 2-chloro-3-(N—methylcarbamoyl) | mesylate | white crystal | 201~205° C. |
| 82 | 3-(4-guanidinobenzoyloxy)-5-(N—methylcarbamoyl) | 2 acetate | colorless solid | ν 3650~2300, 1740, 1690, 1560, 1510, 1400, 1250, 1180, 1125, 1065 cm$^{-1}$ |
| 83 | 3,5-bis(N—ethylcarbamoyl) | mesylate | brown wax | ν 3200, 1735, 1680, 1640, 1560, 1260, 1200, 1050 cm$^{-1}$ |
| 84 | 3,5-bis(N—propylcarbamoyl) | mesylate | yellow bubbly powder | ν 3300, 3150, 1730, 1640, 1560, 1260, 1200, 1040 cm$^{-1}$ |
| 85 | 5-(N—benzylcarbamoyl)-3-(4-guanidinobenzoyloxy) | 2 acetate | colorless solid | ν 3650~2300, 1740, 1700, 1640, 1600, 1570, 1420, 1260, 1190, 1140, 1080 cm$^{-1}$ |
| 86 | 3-chloro-5-{N—(3-pyridyl)carbamoyl} | 2 acetate | pale brown bubbly powder | ν 3400, 3100, 1740, 1680, 1580, 1480, 1420, 1410, 1260, 1080 cm$^{-1}$ |
| 87 | 3-chloro-5-(N,N—dimethylcarbamoyloxy) | acetate | white bubbly powder | ν 3400, 3000, 1730, 1700, 1580, 1440, 1390, 1260, 1160, 1130, 1070 cm$^{-1}$ |
| 88 | 3-chloro-5-(N—ethylcarbamoyloxy) | mesylate | white bubbly powder | ν 3400, 3150, 1730, 1680, 1600, 1570, 1440, 1260, 1200, 1140, 1060 cm$^{-1}$ |
| 89 | 3-sulfamoyl | acetate | white crystal | ν 3430, 1735, 1690, 1570, 1410, 1270, 1210, 1180, 1160, 1075, 1010, 765 cm$^{-1}$ |
| 90 | 3-chloro-4-(N,N—dimethylsulfamoyl) | acetate | yellow bubbly powder | ν 3400, 3000, 1740, 1690, 1570, 1410, 1340, 1250, 1200, 1160, 1060 cm$^{-1}$ |
| 91 | 2-(N,N—diethylsulfamoyl) | mesylate | white powder | ν 3350, 3130, 2980, 1740, 1675, 1600, 1565, 1470, 1330, 1260, 1200, 1055, 1015, 940, 785, 760, 715 cm$^{-1}$ |
| 92 | 3-(N,N—diethylsulfamoyl) | mesylate | white powder | ν 3350, 3150, 2980, 1735, 1680, 1600, 1565, 1465, 1330, 1260, 1200, 1065, 1040, 1015, 935, 780, 760, 715 cm$^{-1}$ |
| 93 | 4-(N,N—diethylsulfamoyl) | mesylate | white crystal | ν 3400, 3130, 1735, 1695, 1565, 1325, 1270, 1205, 1175, 1150, 1075, 1040, 1015, 945, 720 cm$^{-1}$ |

TABLE 2-continued

| Example No. | The Structure of Products (R²)n | HX (Salt) | The Appearance of Products | m.p. and IR Value of Products |
|---|---|---|---|---|
| 94 | 3-chloro-4-(N,N—diethylsulfamoyl) | acetate | pale brown bubbly powder | ν 3400, 2500, 1740, 1680, 1560, 1400, 1250, 1200, 1140, 1060, 1010 cm⁻¹ |
| 95 | 3-chloro-5-(N,N—diethylsulfamoyl) | acetate | pale brown wax | ν 3650~2100, 1050, 1010, 935, 805, 755 cm⁻¹ (neat) |
| 96 | 4-(N,N—diethylsulfamoyl)-2-fluoro | acetate | yellow wax | ν 3400, 3000, 1740, 1680, 1560, 1500, 1410, 1260, 1140, 1070, 1050, 1010 cm⁻¹ |
| 97 | 4-(N,N—dipropyl)sulfamoyl | mesylate | white crystal | ν 3400, 2980, 1735, 1675, 1600, 1575, 1350, 1265, 1205, 1160, 1050 cm⁻¹ |
| 98 | 4-(1-pyrrolidinylsulfonyl) | acetate | pale brown solid | ν 3700~2200, 1740, 1690, 1590, 1510, 1405, 1340, 1265, 1205, 1160, 1100, 1065, 1015 cm⁻¹ |
| 99 | 3-piperidinosulfonyl | acetate | white solid | ν 3650~3000, 2940, 2850, 1740, 1680, 1570, 1405, 1340, 1265, 1205, 1170, 1070 cm⁻¹ |
| 100 | 3-morpholinosulfonyl | acetate | white solid | ν 3650~3000, 2960, 2850, 1740, 1680, 1570, 1405, 1355, 1270, 1210, 1170, 1115, 1070 cm⁻¹ |
| 101 | 4-morpholinosulfonyl | acetate | pale yellow solid | ν 3700~2300, 1740, 1710, 1690, 1570, 1400, 1350, 1270, 1210, 1160, 1120, 1100, 1060, 1020 cm⁻¹ |
| 102 | 3-chloro-5-{N—(4-sulfamoylphenyl)carbamoyl} | acetate | pale brown amorphous | ν 2500~3500, 1720(S), 1660, 1560, 1520, 1400 cm⁻¹ |
| 103 | 3-chloro-5-[N—{4-(N,N—dimethylsulfamoyl)phenyl}carbamoyl] | acetate | white bubbly powder | ν 3400, 1730, 1670, 1570, 1510, 1400, 1320, 1250, 1170, 1150, 1060, 1010, 950, 880, 840, 760, 720, 710 cm⁻¹ |
| 104 | 3-chloro-5-[N—{4-(N,N—diethylsulfamoyl)phenyl}carbamoyl] | acetate | white bubbly powder | ν 3400, 1735, 1680, 1580, 1400, 1320, 1260, 1150, 1070, 1020 cm⁻¹ |
| 105 | 2-chloro-5-(N—mesylamino) | acetate | white crystal | ν 3450, 3100, 2860~2200, 1750, 1695, 1570, 1480, 1405, 1335, 1245, 1175, 1145, 1065, 1050 cm⁻¹ (neat) |
| 106 | 3-chloro-5-(N—ethanesulfonylamino) | acetate | pale yellow bubbly powder | ν 3400, 3150, 1770, 1740, 1680, 1590, 1400, 1260, 1200, 1130, 1070 cm⁻¹ |
| 107 | 3-nitro | mesylate | white crystal | 162~166° C. |
| 108 | 4-nitro | mesylate | pale brown crystal | 228~231° C. |
| 109 | 3-hydroxy-5-methyl | acetate | yellow bubbly powder | ν 2500~3500, 1720, 1680, 1400, 1320, 1260, 1170, 1120 cm⁻¹ |
| 110 | 5-hydroxy-3-methoxy | acetate | colorless solid | ν 3650~2200, 1730, 1690, 1600, 1570, 1410, 1270, 1160, 1130 cm⁻¹ |
| 111 | 5-hydroxy-3-methoxycarbonyl | acetate | pale yellow solid | ν 3650~2300, 1720, 1695, 1600, 1570, 1440, 1410, 1330, 1260, 1145 cm⁻¹ |
| 112 | 3-chloro-5-hydroxy | mesylate | pale brown powder | 170~173° C. |
| 113 | 3-(4-guanidinobenzoyloxy)-5-hydroxy | 2 mesylate | brown bubbly powder | ν 3350, 3150, 1730, 1680, 1600, 1570, 1460, 1400, 1260, 1180, 1120, 1040 cm⁻¹ |
| 114 | 5-hydroxy-3-(N—methylcarbamoyl) | acetate | pale yellow solid | ν 3650~2300, 1720, 1610, 1570, 1410, 1270, 1150 cm⁻¹ |
| 115 | 3-(N—benzylcarbamoyl)-5-hydroxy | acetate | colorless solid | ν 3650~2300, 1740, 1700, 1650, 1600, 1520, 1410, 1340, 1260, 1150, 1080 cm⁻¹ |
| 116 | 3-guanidino | 2 acetate | pale brown bubbly powder | ν 3000~3500, 1720, 1680, 1560, 1390, 1250, 1160, 1060, 1010 cm⁻¹ |
| 117 | 4-guanidino | 2 mesylate | brown bubbly powder | ν 3400, 3150, 1730, 1670, 1620, 1600, 1570, 1510, 1260, 1200, 1040 cm⁻¹ |
| 118 | 2-chloro-5-guanidino | 2 acetate | white solid | ν 3700~2300, 1740, 1690, 1560, 1400, 1260, 1180, 1070, 1015 cm⁻¹ |
| 119 | 5-benzyloxy-3-chloro | acetate | pale brown amorphous | ν 3400, 1580, 1415, 1265, 1140 cm⁻¹ |
| 120 | 3-chloro-5-(4-guanidinophenylthiomethyl) | 2 acetate | pale brown amorphous | ν 3350, 1725, 1670, 1560, 1400, 1250, 1180, 1140, 1070, 1010 cm⁻¹ |
| 121 | 3-chloro-5-(3-pyridyl)oxymethyl | 2 acetate | white bubbly powder | ν 3400, 1740, 1710, 1580, 1410, 1270, 1260, 1180 cm⁻¹ |
| 122 | 3-methoxy-5-(1,1-dioxothiazol-3-yl)carbonyl | acetate | pale gray bubbly powder | ν 3600~2500, 1720, 1660, 1640, 1560, 1400, 1310, 1250 cm⁻¹ |
| 123 | 3-chloro-5-(1,1-dioxothiazol-3- | acetate | white bubbly powder | ν 3600~2700, 1730, 1640, 1570, |

TABLE 2-continued

| Example No. | The Structure of Products (R²)n | HX (Salt) | The Appearance of Products | m.p. and IR Value of Products |
|---|---|---|---|---|
| | yl)carbonyl | ° | | 1400, 1320, 1260, 1240 cm⁻¹ |

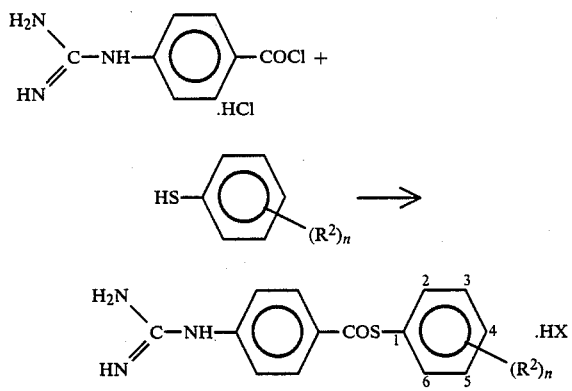

20 ml of hexamethylphospholamide, and 0.58 ml of benzylbromide was added into the mixture. The mixture was stirred for one night.

The reaction mixture was diluted with diethylether, and was washed with water and a saturated aqueous solution of sodium chloride. And the mixture was dried over absolute sodium sulfate, and was concentrated under reduced pressure.

The residue and one g of p-guanidinobenzoyl chloride hydrochloride (prepared by the methods described in Example 1 of each of the specification of Japanese Patent Kokai No. 55-115865 and U.S. Pat. No. 4283418) was stirred for fifteen minutes in pyridine in ice-water bath. Diethylether was added into the reaction mixture, the reaction mixture was decantated, a saturated aqueous solution of sodium bicarbonate was added into insoluble residue and the crystal was filtered off. Further,

TABLE 3

| Example No. | The Structure of Products (R²)n | HX (Salt) | The Appearance of Products | m.p. and IR Value of Products |
|---|---|---|---|---|
| 124 | hydrogen | phosphate | white crystal | 207~210° C. |
| 125 | 2-methyl | mesylate | pale yellow powder | 197~198° C. |
| 126 | 3-methyl | mesylate | white powder | 203~205° C. |
| 127 | 4-methyl | p-tosylate | white crystal | 238~240° C. |
| 128 | 2-methoxy | mesylate | white crystal | 184~186° C. |
| 129 | 3-methoxy | mesylate | white powder | 188~190° C. |
| 130 | 4-methoxy | mesylate | pale yellow powder | 164~165° C. |
| 131 | 4-fluoro | mesylate | pale yellow crystal | 238~241° C. |
| 132 | 2-chloro | mesylate | white powder | 183~184° C. |
| 133 | 3-chloro | mesylate | white crystal | 185~190° C. |
| 134 | 4-chloro | mesylate | white crystal | 213.8~216° C. |
| 135 | 2,5-dichloro | mesylate | white powder | 209~210° C. |
| 136 | 2,6-dichloro | mesylate | white powder | 190~195° C. |
| 137 | 3,4-dichloro | mesylate | white powder | 217~219° C. |
| 138 | 2-bromo | mesylate | white powder | 190~193° C. |
| 139 | 4-carboxy | mesylate | white crystal | 232~233° C. |
| 140 | 4-carboxymethyl | sulfonate | white crystal | 228~232° C. |
| 141 | 2-methoxycarbonyl | mesylate | white powder | 167~169° C. |
| 142 | 4-ethoxycarbonyl | phosphate | white crystal | 188~190° C. |
| 143 | 4-ethoxycarbonyl | mesylate | white crystal | 205~206° C. |
| 144 | 4-ethoxycarbonylmethyl | mesylate | white crystal | 60~65° C. |
| 145 | 4-nitro | mesylate | pale yellow powder | 212~215° C. |
| 146 | 4-(N,N—diethylaminosulfonyl) | mesylate | gray bubbly powder | ν 3400, 3000, 1675, 1560, 1400, 1330, 1260, 1200, 1170, 1150, 1010 cm⁻¹ |

EXAMPLE 147

P-guanidinobenzoic acid 3-carboxy-2-chlorophenylester hydrobromide

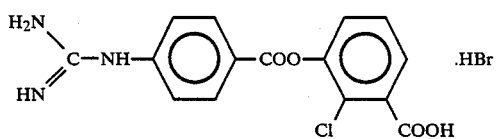

4 ml of 1N sodium hydroxide was added into 700 mg of 3-carboxy-2-chlorophenol, and the mixture was concentrated under reduced pressure to obtain corresponded sodium salt. The sodium salt was dissolved in the crystal was washed with successive, water and acetone, and dried vacuum.

About 5 ml of 30% hydrogen bromide-acetic acid was added into 200 mg of the obtained crystal in an atmosphere of argon, and the mixture was stirred for three hours at ambient temperature. Diethylether was added into the reaction mixture, the precipitated crystal was washed with diethylether, dried in vacuum to give 192 mg of the title compound (yellow powder) having the following physical data:

Melting Point: 220°-227° C.

Hereinafter, by the same procedure as described in Example 147, the compounds of the present invention, Example 148 and Example 149, having the following physical data described in Table 4 were obtained.

TABLE 4

| Example No. | The Structure of Products (R²)n | HX (Salt) | The Appearance of Products | m.p. and IR Value of Products |
|---|---|---|---|---|
| 148 | 3,5-dicarboxy | hydrobromide | yellow powder | 210~214° C. |
| 149 | 2-carboxy-5-chloro | hydrobromide | yellow crystal | bubbly at more than 150° C. (gradually decomposed) |

EXAMPLE 150

P-guanidinobenzoic acid 3-chloro-5-hydroxymethyl-phenyl-ester acetate

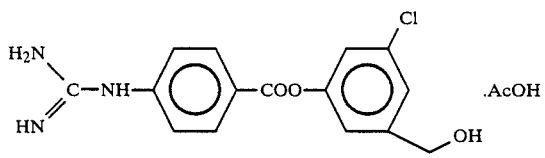

1.970 g of 3-chloro-5-hydroxydbenzoic acid was dissolved in 30 ml of dimethylformamide. 601 mg of sodium hydride was added to the mixture and stirred for ten minutes at ambient temperature.

4.288 g of benzyl bromide was added into the reaction mixture, stirred for two hours at ambient temperature. 30 ml of ethyl acetate was added into the reaction mixture, further the reaction mixture was washed with water at several times. The mixture was dried with absolute magnesium sulfate, and concentrated under reduced pressure. The obtained residue was purified by column chromatography on silica-gel (elusion solvent, hexane: ethyl acetate=10:1) to give 3.61 g of 3-chloro-5-benzyloxybenzoic acid benzylester having the following physical data;

TLC (hexane: ethyl acetate=10:1): Rf 0.26.

3.61 g of the benzyl compound was dissolved in 50 ml of tetrahydrofuran. 579 mg of lithiumaluminiumhydride was added into the mixture, reacted for two hours at ambient temperature. Ethyl acetate was added into the reaction mixture to analyse the excess reagent. The mixture was poured into 1N sodium hydroxide. The reaction mixture was extracted with diethylether, and the extract was dried over absolute magnesium sulfate and concentrated under reduced pressure. The residue was purified by column chromatography on silica-gel (elusion solvent, dichloromethane) to give 1.502 g of 3-chloro-5-benzyloxy-benzylalcohol having the following physical data;

TLC (chloroform: methanol=10:1): Rf 0.69.

1.502 g of the alcohol compound was dissolved in 20 ml of dichloromethane. 655 mg of 2,3-dihydropyran and catalytic amount of p-toluenesulfonic acid were added thereto, and the mixture was reacted for one hour at ambient temperature.

A little amount of pyridine was added into the reaction mixture, and the mixture was washed with water, and concentrated under reduced pressure.

The obtained residue was purified by column chromatography on silica-gel (elusion solvent, hexane: ethyl acetate=10:1) to give 1.83 g of 3-chloro-5-benzyloxybenzylalcohol-0-(2-tetrahydropyranyl)ether having the following physical data;

TLC (hexane: ethyl acetate=10:1): Rf 0.20.

996 mg of obtained the benzyl compound was dissolved in 7 ml of ethyl acetate, this solution was reacted for eliminating benzyl group using 10% palladium carbon as catalyst at the atmospheric temperature and pressure and under an atmosphere of hydrogen. After three hours, the reaction was stopped, the obtained crude product was purified by column chromatography on silica-gel (elusion solvent, hexane: ethyl acetate=5:1) to give 274 mg of 3-chloro-5-(2-tetrahydropyranyloxymethyl)phenol having the following physical data;

TLC (hexane: ethyl acetate=5:3): Rf 0.24.

274 mg of the phenol compound was dissolved in 3 ml of pyridine, 396 mg of p-guanidinobenzoyl chloride hydrochloride was added into the mixture and reacted for two hours at ambient temperature.

20 ml of diethylether was added into the reaction mixture, the precipitate was filtered off. And further, the precipitate was washed with diethylether. An aqueous solution of sodium bicarbonate was added into the insoluble residue, and the produced carbonate was filtered off.

The crude carbonate was dissolved in 3 ml of 60% acetic acid, reacted for two hours at 37° C.

Acetic acid was distilled off under reduced pressure, the residue was purified by column chromatography on silica-gel (elusion solvent, chloroform: methanol: acetic acid=10:2:1) to give 100 mg of the title compound having the following physical data;

TLC (chloroform: methanol: acetic acid=10:2:1): Rf 0.26.

NMR (CD₃OD): δ 8.2 (2H, d, J=8Hz), 7.42 (2H, d, J=8Hz), 7.30 (1H, bs), 7.16 (2H, bs), 4.64 (2H, s).

EXAMPLE 151

P-guanidinobenzoic acid 3-chloro-5-(4-morpholinosulfonyl)phenoxymethylphenylester acetate

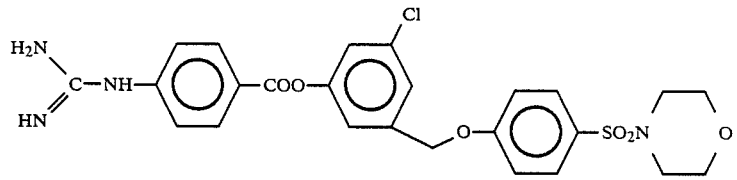

4.04 mg of 3-chloro-5-hydroxybenzoic acid was dissolved in 10 ml of dichloromethane, and 256 mg of 2,3-dihydropyran was added into the mixture. The catalytic amount of p-toluenesulfonic acid was added thereto, and the mixture was reacted for one hour at ambient temperature.

A little amount of pyridine was added into the reaction mixture, and the obtained mixture was washed with water, dried over absolute magnesium sulfate, and concentrated under reduced pressure to give the corresponded (2-tetrahydropyranyl) ether.

The obtained crude product was used in the next reaction without purifying.

That is, the crude product was dissolved in 10 ml of tetrahydrofuran, and cooled in the ice-water bath. 133 mg of lithiumalminiumhydride was added thereto, and the mixture was stirred. The reaction temperature was rised to ambient temperature, and the mixture was further reacted for one hour. Ethyl acetate was added into the reaction mixture to analyse the excess reagent.

The reaction mixture was poured into 20 ml of 1N sodium hydroxide. The mixture was extracted with ethyl acetate, and the extract was concentrated under reduced pressure. The residue was purified by column chromatography or silica-gel (elusion solvent, hexane: ethyl acetate=5:2) to give 541 mg of 3-chloro-5-(2-tetrahydropyranyloxy)benzylalcohol having the following physical data;

TLC (hexane: ethyl acetate=5:3): Rf 0.5.

484 mg of the alcohol thus obtained was dissolved in 10 ml of dichloromethane. 242 mg of triethylamine was added thereto and the mixture was cooled in ice-water bath. Further 273 mg of methanesulfonylchloride was added dropwise to the mixture. After the reaction temperature was rised to ambient temperature, the mixture was washed with water, dried over absolute magnesium sulfate, and concentrated under reduced pressure to give the correspond mesylate.

The obtained crude product was used to the next reaction without purifying. 460 mg of p-morpholinosulfonylphenol was dissolved into the mixture of 7 ml of tetrahydrofuran and 1 ml of hexamethylphosphoramide. 57.6 mg of sodium hydride was added thereto, and the mixture was stirred for ten minutes.

Secondly, mesylate obtained above was added into this reaction solution, reacted for one hour at ambient temperature.

Water was added into the reaction mixture, and the mixture was extracted with ethyl acetate. The extract was washed with water, dried over absolute magnesium sulfate, and concentrated under reduced pressure.

The obtained crude product was dissolved in the mixture solvent of 5 ml of methanol and 5 ml of tetrahydrofuran. Further, 50 mg of p-toluenesulfonic acid was added into the mixture, reacted for two hours at ambient temperature to distill off the solvent. The residue was purified by column chromatography on silica-gel (hexane: ethyl acetate=5:3) to give 228 mg of 3-chloro-5-(4-morpholinosulfonyl)phenoxymethylphenol having the following physical data;

TLC (hexane: ethyl acetate=5:3): Rf 0.18.

By using 228 mg of the phenol compound thus obtained, 207 mg of p-guanidinobenzoyl chloride hydrochloride and 3 ml of pyridine, the esterification was carried out by the same procedure as described in Example 1.

The product was purified by column chromatography on silica-gel (elusion solvent, ether acetate: acetic acid: water=400:100:30) to give 150 mg of title compound having the following physical data;

TLC (chloroform: methanol: acetic acid=10:2:1): Rf 0.7.

IR: ν 3600–2500, 1720, 1680, 1560, 1400, 1330 cm⁻¹.

EXAMPLE 152 p-guanidinobenzoic acid 3-methoxy-5-(4-morpholinosulfonyl)phenoxymethylphenylester acetate

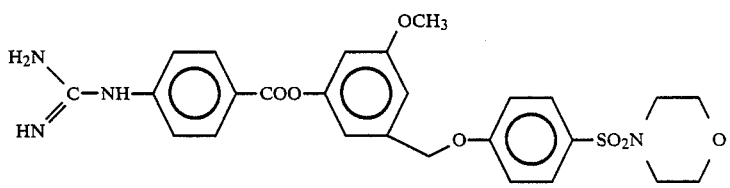

By the same procedure as described in Example 151, the title compound (white powder) having the following physical data was obtained.

TLC (ethyl acetate: acetic acid: water=400:100:30): Rf 0.72.

IR: ν 2500–3600, 1720, 1680, 1590, 1400, 1340 cm⁻¹.

PREPARATIVE EXAMPLE 1

10 g of p-guanidinobenzoic acid 3-chloro-5-hydroxyphenyl ester methanesulfonate (prepared in Example 112), 400 mg of cellulose calcium gluconate (disintegrator), 200 mg of magnesium stearate (lubricator) and 9.4 g of microcrystalline cellulose were admixed and punched out in conventional manner to give 100 tablets each containing 100 mg of the active ingredient.

PREPARATIVE EXAMPLE 2

One g of p-guanidinobenzoic acid 3-chloro-5-hydroxyphenyl ester methanesulfonate (prepared in Example 112) was dissolved in 10 ml of ethanol and the solution was sterilized by filtration through a bacteria-retaining filter, and placed 0.5 ml portions into 5 ml ampoules to obtain ampoules each containing 50 mg of the active ingredient, and the ampoules were then sealed. The contents of ampoules are used for injection by diluting with a trishydrochloric acid buffer solution (pH 8.6) to 2.5 ml.

PREPARATIVE EXAMPLE 3

10 g of p-guanidinobenzoic acid 3-chloro-5-ethanesulfonyloxyphenyl ester acetate (prepared in Example 75), 400 mg of cellulose calcium gluconate (disintegrator), 200 mg of magnesium stearate (lubricator) and 9.4 g of microcrystalline cellulose were admixed and punched out in conventional manner to give 100 tablets each containing 100 mg of the active ingredient.

PREPARATIVE EXAMPLE 4

One g of p-guanidinobenzoic acid 3-chloro-5-ethanesulfonyloxyphenyl ester acetate (prepared in Example 75), was dissolved in 10 ml of ethanol and the solution was sterilized by filtration through a bacteria-retaining filter, and placed 0.5 ml portions into 5 ml ampoules to obtain ampoules each containing 50 mg of the active ingredient, and the ampoules were then sealed. The contents of ampoules are used for injection by diluting with a tris-hydrochloric acid buffer solution (pH 8.6) to 2.5 ml.

PREPARATIVE EXAMPLE 5

10 g of p-guanidinobenzoic acid 2,5-dichlorothiophenyl ester methanesulfonate (prepared in Example 135), 400 mg of cellulose calcium gluconate (disintegrator), 200 mg of magnesium stearate (lubricator) and 9.4 g of microcrystalline cellulose were admixed and punched out in conventional manner to give 100 tablets each containing 100 mg of the active ingredient.

PREPARATIVE EXAMPLE 6

One g of p-guanidinobenzoic acid 2,5-dichlorothiophenyl ester methanesulfonate (prepared in Example 135) was dissolved in 10 ml of ethanol and the solution was sterilized by filtration through a bacteria-retaining filter, and placed 0.5 ml portions into 5 ml ampoules to obtain ampoules each containing 50 mg of the active ingredient, and the ampoules were then sealed. The contents of ampoules are used for injection by diluting with a suitable quantity of dilution, for example, by diluting with a trishydrochloric acid buffer solution (pH 8.6) to 2.5 ml.

What we claim:

1. A derivative of p-guanidinobenzoic acid of the formula:

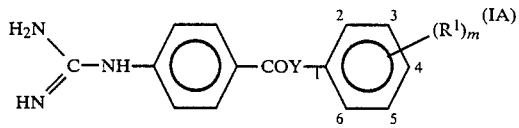

wherein Y represents an oxygen atom and $(R^1)_m$ represents a member selected from the group consisting of 5-ethanesulfonyloxy-3-methoxymethyl, 5-mesyloxy-3-methoxy, 3-chloro-5-mesyloxy, 3-chloro-5-ethanesulfonyloxy, 3-chloro-5-isopropanesulfonyloxy, 5-benzenesulfonyloxy-3-chloro and 5-ethanesulfonyloxy-3-methyl group, or an acid addition salt thereof.

2. A pharmaceutical composition for the treatment and/or prevention of diseases induced by abnormal enhancing of degradation of proteins by the action of elastase in mammals, comprising;

(a) a derivative of p-guanidinobenzoic acid of the formula:

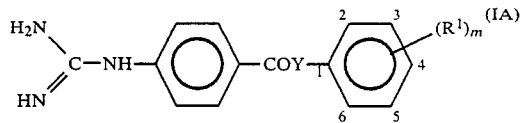

wherein Y represents an oxygen atom and $(R^1)_m$ represents a member selected from the group consisting of 5-ethanesulfonyloxy-3-methoxymethyl, 5-mesyloxy-3-methoxy, 3-chloro-5-mesyloxy, 3-chloro-5-ethanesulfonyloxy, 3-chloro-5-isopropanesulfonyloxy, 5-benzenesulfonyloxy-3-chloro and 5-ethanesulfonyloxy-3-methyl group, or an acid addition salt thereof, and (b) at least one pharmaceutically acceptable ingredient.

3. A method for the treatment and/or prevention of diseases induced by abnormal enhancing of degradation of proteins by the action of elastase in mammals subject to or suffering therefrom, comprising administering an effective amount of at least one p-guanidinobenzoic acid of the formula:

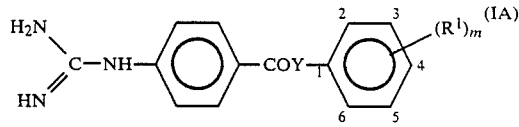

wherein Y represents an oxygen atom and $(R^1)_m$ represents a member selected from the group consisting of 5-ethanesulfonyloxy-3-methoxymethyl, 5-mesyloxy-3-methoxy, 3-chloro-5-mesyloxy, 3-chloro-5-ethanesulfonyloxy, 3-chloro-5-isopropanesulfonyloxy, 5-benzenesulfonyloxy-3-chloro and 5-ethanesulfonyloxy-3-methyl group, or an acid addition salt thereof.

* * * * *